US008017389B2

(12) United States Patent
Phillips et al.

(10) Patent No.: US 8,017,389 B2
(45) Date of Patent: Sep. 13, 2011

(54) ENRICHED STEM CELL AND PROGENITOR CELL POPULATIONS, AND METHODS OF PRODUCING AND USING SUCH POPULATIONS

(75) Inventors: Michael Ian Phillips, Claremont, CA (US); Yao Liang Tang, Pomona, CA (US)

(73) Assignee: Keck Graduate Institute, Claremont, CA (US)

( * ) Notice: Subject to any disclaimer, the term of this patent is extended or adjusted under 35 U.S.C. 154(b) by 760 days.

(21) Appl. No.: 11/983,431

(22) Filed: Nov. 7, 2007

(65) Prior Publication Data

US 2008/0213230 A1    Sep. 4, 2008

Related U.S. Application Data

(60) Provisional application No. 60/857,661, filed on Nov. 7, 2006.

(51) Int. Cl.
*C12N 5/00* (2006.01)
(52) U.S. Cl. ........ 435/325; 435/375; 435/377; 424/93.1
(58) Field of Classification Search ........................ None
See application file for complete search history.

(56) References Cited

U.S. PATENT DOCUMENTS

| | | | |
|---|---|---|---|
| 6,239,117 B1 * | 5/2001 | Christ et al. ................. | 514/44 R |
| 6,673,904 B2 * | 1/2004 | Nishikawa et al. ........... | 530/399 |
| 2003/0166276 A1 * | 9/2003 | Carpenter ..................... | 435/368 |
| 2005/0159416 A1 * | 7/2005 | Morgan et al. ............. | 514/232.5 |

FOREIGN PATENT DOCUMENTS

WO    WO 2004/019767 A2    3/2004

OTHER PUBLICATIONS

Demoulin JB et al. Ly-6A/E induction by interleukin-6 and interleukin-9 in T cells. Eur Cytokine Netw 10: 49-56.*
Castro RF et al. 2002. Failure of bone marrow cells to transdifferentiate into neural cells in vivo. Science 297: 1299.*
Mezey E et al. and Castro RF et al. 2003. "Comment on Failure of bone marrow cells to transdifferentiate into neural cells in vivo" and "Response to Comment on FFailure of bone marrow cells to transdifferentiate into neural cells in vivo", Science 299: 1184b,c.*
Reinecke H et al. 2002. Skeletal muscle stem cells do not transdifferentiate into cardiomyocytes after cardiac grafting. J Mol Cell Cardiol 34: 241-249.*
Murry CE et al. 2004. Hematopoietic stem cells do not transdifferentiate into cardiac myocytes in myocardial infarcts. Natrue 428: 664-668.*
Yoshitaka, Iso et al., "Factors secreted by adult human bone marrow Stem/Progenitor cells activate and protect adult cardiac Stem/Progenitor cells," Database Accession No. PREV200700122045; *Circulation 114*(18) Suppl. S:298, Oct. 31, 2006.
Beltrami, Antonio P., et al., "Adult Cardiac Stem Cells Are Multipotent and Support Myocardial Regeneration," *Cell 114*:763-776, Sep. 19, 2003.
Braunwald, Eugene, et al., "Congestive Heart Failure: Fifty Years of Progress," *Circulation 102*:IV-14-IV-23, 2000.
Camelliti, Patrizia, et al., "Structural and functional characterisation of cardiac fibroblasts," *Cardiovascular Research 65*:40-51, 2005.
Fukuda, Keiichi, et al., "Stem Cells as a Source of Regenerative Cardiomyocytes," *Circulation Research 98*:1002-1013, 2006.
Gude, Natalie, et al, "Akt Promotes Increased Cardiomyocyte Cycling and Expansion of the Cardiac Progenitor Cell Population," *Circulation Research 99*:381-388, 2006; Online Supplemental Information, downloaded from circres.ahajournals.org on Apr. 6, 2009, 3 pages.
Laugwitz, Karl-Ludwig, et al., "Postnatal isl1+ cardioblasts enter fully differentiated cardiomyocyte lineages," *Nature 433*:647-653, Feb. 10, 2005.
Martin, Cindy M., et al., "Persistent expression of the ATP-binding cassette transporter, Abcg2, identifies cardiac SP cells in the developing and adult heart," *Developmental Biology 265*:262-275, 2004.
Orlic, Donald, et al., "Stem Cells for Myocardial Regeneration," *Circulation Research 91*:1092-1102, 2002.
Sakai, T., et al., "Fetal cell transplantation: a comparison of three cell types," *Journal of Thoracic Cardiovascular Surgery 118*(4):715-724, Oct. 1999 (Abstract).
Tang, Yao Liang, et al., "Autologous mesenchymal stem cell transplantation induce VEGF and neovascularization in ischemic myocardium," *Regulatory Peptides 117*:3-10, 2004.
Tang, Yao Liang, et al., "Improved Graft Mesenchymal Stem Cell Survival in Ischemic Heart With a Hypoxia-Regulated Heme Oxygenase-1 Vector," *Journal of the American College of Cardiology 46*(7):1339-1350, 2005.
Tang, Yao Liang, et al., "Paracrine Action Enhances the Effects of Autologous Mesenchymal Stem Cell Transplantation on Vascular Regeneration in Rat Model of Myocardial Infarction," *Ann Thorac Surg 80*:229-237, 2005.
Tang, Y.L., "Cellular therapy with autologous skeletal myoblasts for ischemic heart disease and heart failure," *Methods Mol Med. 112*:193-204, 2005 (Abstract).
Tomita, Yuichi, et al., "Cardiac neural crest cells contribute to the dormant multipotent stem cell in the mammalian heart," *The Journal of Cell Biology 170*(7):1135-1146, Sep. 26, 2005.
Wang, Xiaohong, et al., "The Role of the Sca-1+/CD31—Cardiac Progenitor Cell Population in Postinfarction Left Ventricular Remodeling," *Stem Cells 24*:1779-1788, 2006.

(Continued)

*Primary Examiner* — Lora E Barnhart
(74) *Attorney, Agent, or Firm* — Seed IP Law Group PLLC

(57) ABSTRACT

The present invention provides a novel method to isolate and expand pure progenitor/stem cells from a primary tissue explant, which produces a population enriched in multipotent functional progenitor/stem cells free of contaminating fibroblasts and other cell types. Cardiac progenitor/stem cells isolated by this method maintain their self-renewal and clonogenic character in vitro and differentiate into normal cells in myocardium, including cardiomyocytes, endothelial cells, and smooth muscle cells, after transplantation into ischemic hearts. The present invention also includes substantially pure populations of multipotent progenitor/stem cells, e.g., cardiac progenitor/stem cells, and their use to treat and prevent diseases and injuries, including those resulting from myocardial infarction.

7 Claims, 8 Drawing Sheets
(5 of 8 Drawing Sheet(s) Filed in Color)

OTHER PUBLICATIONS

Williams, R. Lindsay, et al., "Myeloid leukaemia inhibitory factor maintains the developmental potential of embryonic stem cells," *Nature 336*:684-687, Dec. 15, 1988.

Xu, Meifeng, et al., "Differentiation of Bone Marrow Stromal Cells Into the Cardiac Phenotype Requires Intercellular Communication With Myocytes," *Circulation 110*:2658-2665, 2004.

Yamada, Yoshihiro., et al., "Cardiac progenitor cells in brown adipose tissue repaired damaged myocardium," *Biochemical and Biophysical Research Communications 342*:662-670, 2006.

Matsuura et al., "Adult Cardiac Sca-1-positive Cells Differentiate into Beating Cardiomyocytes," The Journal of Biological Chemistry 279(12):11384-11391, Mar. 19, 2004.

Messina et al., "Isolation and Expansion of Adult Cardiac Stem Cells From Human and Murine Heart," Circulation Research, 95:911-921, Oct. 29, 2004, downloaded from circres.ahajournals.org at European Patent Office on Apr. 18, 2008.

Oh et al., "Cardiac progenitor cells from adult myocardium: Homing, differentiation, and fusion after infarction," PNAS 100(21): 12313-12318, Oct. 14, 2003.

Tang et al., "A novel two-step procedure to expand cardiac Sca-1+ cells clonally," Biochemical and Biophysical Research Communications 359:877-883, 2007.

Kurata et al., "Stem cell factor induces proliferation and differentiation of fetal progenitor cells in the mouse," *British Journal of Haematology*, 101:676-687, 1998.

Roodman et al., "Expression of Latent Hematopoietic Progenitor Cells in Cultures of Newborn and Adult Baboon Liver," *Blood*, 65(6):1518-1525, 1985.

* cited by examiner

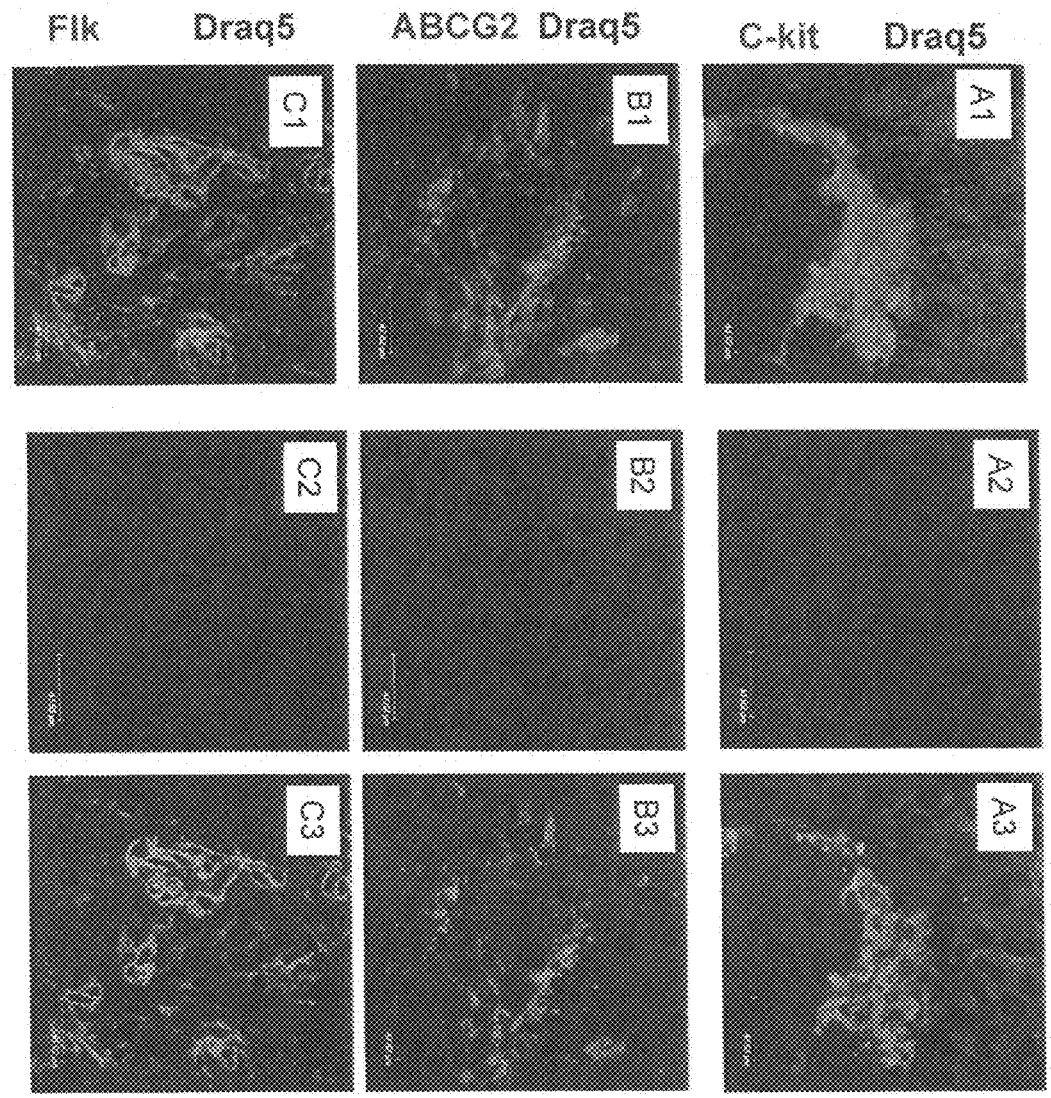
FIGURES 3A1-3C3

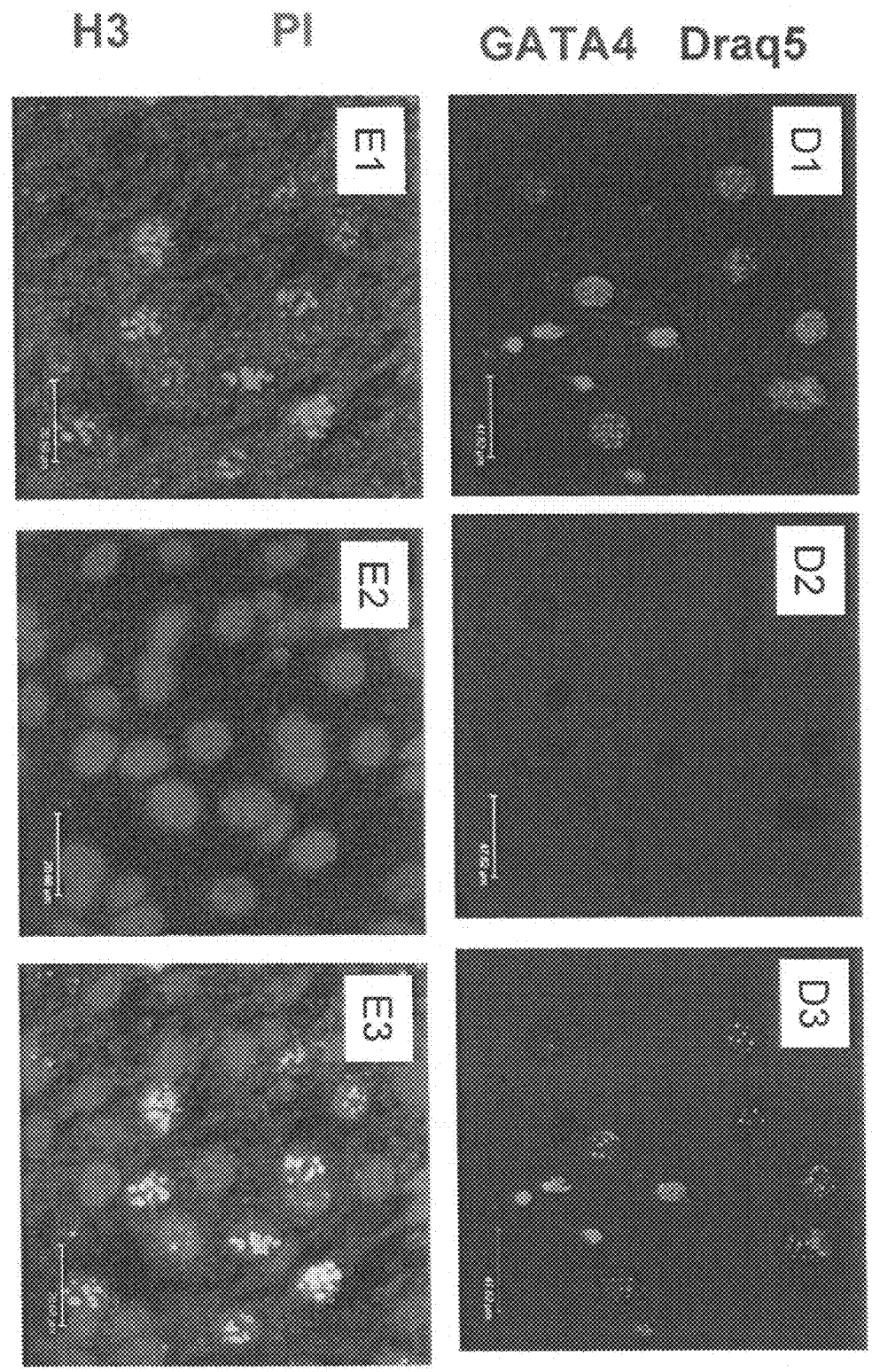
FIGURES 3D1-3E3

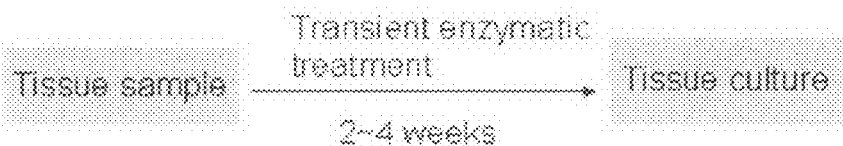
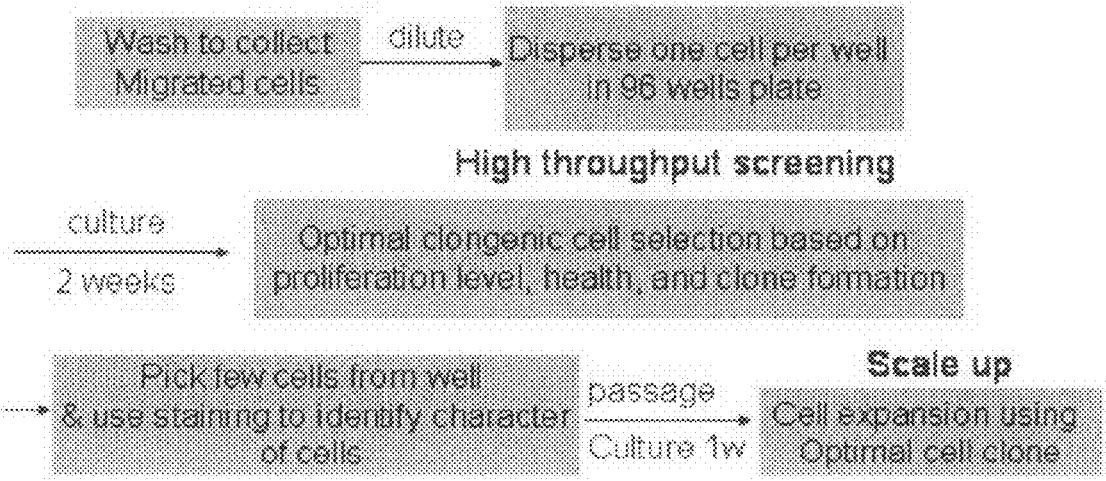
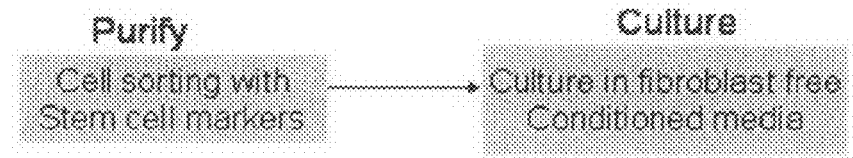
FIG. 6

ENRICHED STEM CELL AND PROGENITOR CELL POPULATIONS, AND METHODS OF PRODUCING AND USING SUCH POPULATIONS

CROSS-REFERENCE TO RELATED APPLICATION

This application claims the benefit under 35 U.S.C. §119 (e) of U.S. Provisional Patent Application No. 60/857,661 filed Nov. 7, 2006, where this provisional application is incorporated herein by reference in its entirety.

STATEMENT OF GOVERNMENT INTEREST

This invention was made with government support under Grant No. NIH 1RO1 HL 077602-01 awarded by the National Institutes of Health. The government may have certain rights in this invention.

BACKGROUND OF THE INVENTION

1. Field of the Invention

The present invention relates to highly purified populations of multipotent mammalian stem cells and progenitor cells, including cardiac stem cells and progenitor cells having the capacity for expansion and differentiation into cardiomyocytes, endothelial cells or smooth muscle cells. The present invention further relates to methods of isolating and expanding multipotent mammalian stem cells and progenitor cells, and therapeutic uses thereof.

2. Description of the Related Art

Ischemic heart disease accounts for 50% of all cardiovascular deaths and is the leading cause of congestive heart failure (reference 1). A new approach to cardiac repair is cellular therapy with stem cells, such as bone marrow-derived mesenchymal stem cells (references 2-4), skeletal myoblast (reference 5), adipose derived mesenchymal stem cells (reference 6), and hematopoietic stem cells (reference 7). Recently, resident cardiac progenitor/stem cells (CSCs) were discovered in the adult heart (references 8-13). Resident CSCs are characterized by their capacity to self-renew in culture, and are multi-potent for forming normal cell types in hearts. Accordingly, they hold great promise for clinical applications, because they are normal components of adult heart and capable of differentiating into cardiomyocyte or vascular lineages.

Previously, populations of cardiac stem cells (c-kit+, Sca-1+) were isolated from adult hearts by cell sorting from enzymatically digested hearts based on cell surface markers (references 8, 9, and 11). However, enzymatic digestion of myocardium compromises the integrity of important surface antigens of resident CSCs and leads to dysfunctional sorted cells, which makes the method hard to be reproduced. More recently, Messina et al. (reference 10) demonstrated that some CSCs migrated from human myocardial biopsies could form cardiospheres that expressed Sca-1, c-kit, Flk, and CD31. However, these cardiospheres contained a mixture of cells, including cardiac fibroblasts, which grow faster than endogenous cardiac stem cells in the cardiosphere. Contamination of resulting cardiospheres with fibroblasts limits the therapeutic use of CSCs prepared from explants, because the contaminating fibroblasts are less efficient for heart repair and may facilitate the scar dilation (reference 14).

Accordingly, there is a need in the art for purified CSCs and substantially free of other cell types, including fibroblasts, as well as improved methods of isolating and expanding multipotent mammalian stem cells and progenitor cells.

BRIEF SUMMARY OF THE INVENTION

The present invention provides novel methods of purifying stem cells and progenitor cells from a tissue sample, resulting in a cell population greatly enriched in functional stem cells and progenitor cells. These cell populations may be used for a variety of therapeutic uses, including the reconstitution of injured, dead, or diseased tissue. The methods of the invention may be used to purify stem cells from any tissue, including, e.g., cardiac, brain, kidney, liver, skin, umbilical cord matrix, etc., at any stage of development. In certain embodiments, the tissue sample is obtained from a juvenile or adult mammal, and, particularly, a human.

In one embodiment, the present invention provides a method of preparing an isolated cell population enriched in stem cells or progenitor cells, comprising culturing a tissue sample; obtaining cells that migrate above adherent fibroblasts during said culturing; cloning one or more cells obtained to produce one or more clonogenic populations; isolating stem cells or progenitor cells from one or more clonogenic populations obtained by cell sorting using one or more cell surface or internal markers of stem cells or progenitor cells; and culturing the isolated stem cells or progenitor cells in conditioned media in the absence of feeder cells; thereby obtaining an isolated cell population enriched in stem cells or progenitor cells.

In one embodiment, the tissue is cardiac tissue. In another embodiment, the tissue is adult mammalian tissue (e.g., adult human tissue).

In one embodiment, the tissue sample is subjected to enzymatic dissociation. In another embodiment, the tissue is cultured for a time sufficient to allow fibroblasts present in the tissue to adhere. Thus, in various embodiments, the tissue is cultured for at least one week, at least 10 days, at least two weeks, or at least three weeks.

In certain embodiments, the methods are performed using an agent that binds a cell surface or internal marker of stem cells selected from the group consisting of: Sca-1, c-Kit, ATP-binding cassette transporter, B1-3, Flk-1, CD31, CD34, Isl1, GATA4, Nkx2.5, and the markers listed in Table 1.

In particular embodiments of these methods, the stem cells or progenitor cells are cultured in the absence of additional cells, such as feeder cells or support cells. In one embodiment, the stem cells or progenitor cells are cultured in cell growth medium comprising conditioned medium, which may be fibroblast-conditioned medium. In related embodiment, the isolated stem cells or progenitor cells are cultured in cell growth medium supplemented with fibroblast growth factor, heregulin, IGF-1, activin A, SB203580, or BIO.

In certain embodiments, the cell population isolated using the methods provided herein contains at least 90% stem or progenitor cells.

In another aspect, the present invention provides an isolated population of mammalian tissue-derived cells, wherein at least 90% of the cells are stem cells or progenitor cells capable of undergoing differentiation.

In one embodiment, at least 90% of the cells are cardiac stem cells or cardiac progenitor cells. In particular embodiments, the cardiac stem cells and cardiac progenitor cells are capable of differentiating into one or more cells selected from the group consisting of: cardiomyocytes, endothelial cells, smooth muscle cells, and cardiac neural crest cells. In one embodiment, at least 90% of the cells are Sca-1+. In a related embodiment, at least 50% of the cells express GATA4 or Nkx2.5.

The present invention further includes an isolated cell population enriched in stem cells or progenitor cells prepared according to a method of the present invention.

In a further related aspect, the present invention also includes a method of preparing an isolated population of differentiated cells comprising: preparing an isolated cell population enriched in stem cells or progenitor cells according to a method of the present invention; and inducing the stem cells or progenitor cells to differentiate. In one embodiment, the differentiated cells include cardiomyocytes, endothelial cells, smooth muscle cells, and cardiac neural crest cells. The cardiac stem cells and progenitor cells may be induced to differentiate by exposure to a differentiation factor. The differentiation factor may be, e.g., a member of the transforming growth factor β superfamily, such as transforming growth factor β, bone morphogenic protein 2, bone morphogenic protein 4, and activin A.

The present invention further provides a pharmaceutical composition comprising an isolated cell population according to the present invention and a biologically compatible carrier or excipient, such as 5-azacytidine, cardiogenol C, and ascorbic acid.

The present invention also includes methods of treating or preventing a tissue injury, comprising providing a pharmaceutical composition of the present invention to a patient having an injured tissue or at risk of tissue injury. In a related embodiment, the present invention includes a method of treating a patient diagnosed with a cardiac injury or disease, comprising providing the pharmaceutical composition of the invention to said patient. In another related embodiment, the present invention provides a method of reconstituting cardiac tissue comprising providing a pharmaceutical composition of the present invention to injured or dead cardiac tissue. In one embodiment, the cardiac tissue is myocardium. In another embodiment, the pharmaceutical composition comprises cardiac stem cells and/or cardiac progenitor cells. In particular embodiments, the cardiac injury or disease is myocardial infarct, left ventricular hypertrophy, right ventricular hypertrophy, emboli, heart failure, congenital heart deficit, heart valve disease, arrhythmia, or myocarditis. In certain embodiments, the biological sample is obtained from the patient to be treated.

In a further aspect, the present invention provides a kit useful for the preparation of an isolated cell population enriched in stem cells or progenitor cells, comprising an agent that binds a cell surface, or an internal, marker of stem cells or progenitor cells and conditioned medium.

In certain embodiments, the kit is useful for the preparation of an isolated cell population enriched in cardiac stem cells or progenitor cells, and comprises an agent that binds a cell surface, or an internal, marker of cardiac stem cells or progenitor cells and conditioned medium for cardiac stem cells or progenitor cells.

In a related aspect, the present invention provides a kit useful for reconstituting cardiac tissue, comprising purified cardiac stem cells or cardiac progenitor cells, and a vector with a reporter gene (e.g., GFP) under the control of a cardiac specific promoter (e.g., GATA4 promoter).

In another aspect, the present invention provide a method of preparing a cell population enriched in stem cells or progenitor cells, comprising: (a) culturing a tissue sample following transient enzymatic treatment to facilitate the release of stem cells or progenitor cells; (b) obtaining cells that migrate above adherent cells during said culturing; (c) cloning one or more cells obtained in (b) to produce one or more clonogenic populations, by culturing the cells obtained in (b) at a one cell or one cell clone per well ratio; (d) identifying a clonogenic population produced in (c) that proliferates and expresses one or more stem cell or differentiation markers; (e) culturing the clonogenic population identified in (d); (f) isolating stem cells or progenitor cells from the clonogenic population cultured in (e) by cell sorting using one or more cell surface (or internal) markers of stem cells or progenitor cells; and (g) culturing the isolated stem cells or progenitor cells in conditioned media in the absence of feeder cells; thereby obtaining an isolated cell population enriched in stem cells or progenitor cells.

In yet another aspect, the present invention provides a method of determining whether a tissue sample contains tissue-specific stem cells or progenitor cells, comprising: culturing a tissue sample; obtaining cells that migrate above adherent cells during said culturing; diluting and culturing the cells obtained at a one cell or one cell clone per well ratio; identifying cells that proliferate; and determining whether a cell that proliferates expresses one or more cell surface (or internal) markers of stem cells or progenitor cells and one or more tissue-specific markers, thereby determining whether the tissue sample contains tissue-specific stem cells or progenitor cells.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIGS. 1A-1G are micrographs of cells: FIG. 1A shows phase-contrast microscopy of cells migrated from a primary culture of a mouse ventricular explant; FIG. 1B shows migrated cells aggregated and proliferated above the coating of fibroblasts (white arrow indicates new round bright cells migrated off the explant; green arrow indicates fibroblast layer); FIG. 1C shows a culture of purified Sca-1+ cells after MACS enrichment; and FIG. 1D shows spheres formed from isolated Sca-1+ cells. FIGS. 1E-G show a single Sca-1+ cell forming a sphere without cardiac fibroblastic cells at the periphery (X20), at three different time points (E=0 days; F=10 days; and G=three weeks).

FIGS. 3A1-3E3 show immunofluorescent images of purified Sca-1+ cells grown on coated wells and counterstained with Draq5 (blue) or PI (red). Cells were stained using primary antibodies specific for stem cell markers, c-kit (A) and ABCG2 (B); an endothelial cell marker, FLK-1 (C); GATA4 (D), a cardiac specific transcription factor; and phosphor-H3 (E), a marker of mitotic Cdc2 activity. A1-E1 show antibody-specific staining; A2-E2 show draq5 or PI counterstaining; and A3-E3 show both antibody-specific staining and counterstaining.

FIGS. 4A and 4B show the sphere stained with anti-myosin (red; A) or anti-connexin 43 (green; B). FIG. 4C shows the sphere counterstained with Draq5 (blue), and FIG. 4D shows the sphere stained with both anti-connexin 43 and anti-myosin and counterstained with Draq5.

FIG. 5A shows β-gal-expressing Sca-1+ cells. β-gal staining in vitro demonstrated that most of cells express β-gal. FIG. 5B provides merged images of double staining of sections for β-gal (green) and the cardiac-specific protein, cTnI (red), which demonstrate the colocalization of reporter with cardiac-specific protein (yellow). FIGS. 5C-D provide merged images of double staining of sections for β-gal (green) and either CD31 (red; C) or SM-α-actin (red; D), which demonstrate that Sca-1+ cells integrated into new blood vessels (yellow). The arrows indicate grafted LacZ-labeled Sca-1+ cells.

FIG. 6 is a diagram depicting one embodiment of a method of the present invention for purifying, expanding, and isolating stem cells and progenitor cells, to prepare a purified cell population enriched in stem cells and progenitor cells.

DETAILED DESCRIPTION OF THE INVENTION

Figures 1A, 1B, 1C, 1D, 1E, 1F, 1G:
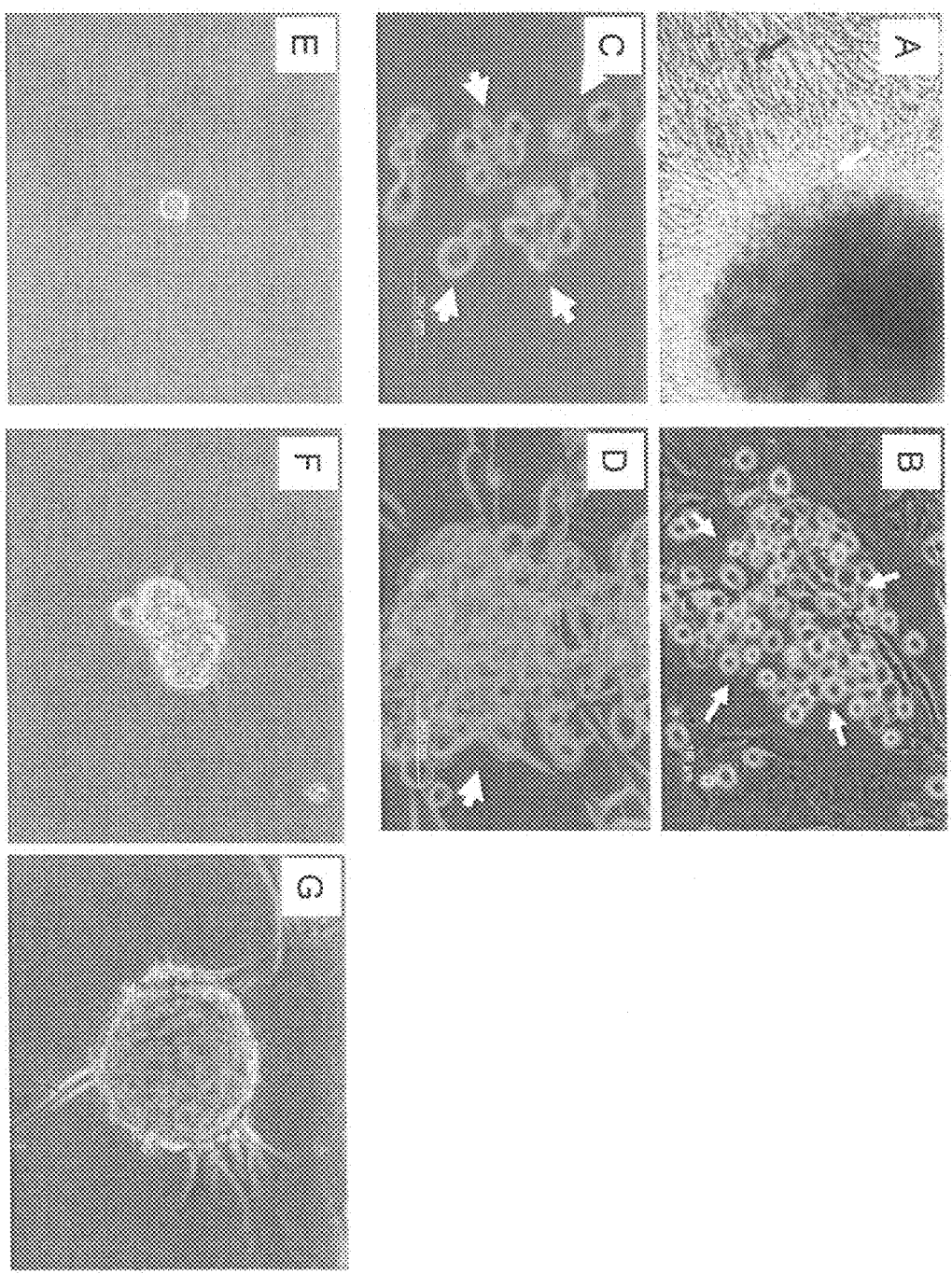
FIGS. 1A-1G depict morphological and growth characteristics of Sca-1+ cells derived from heart tissue.

The present invention provides novel methods for purifying and expanding multipotent stem cells and progenitor cells from mammalian tissues. These methods may be used to prepare a substantially pure population of stem cells and progenitor cells, essentially free of other contaminating cell types, from a tissue sample obtained from a patient or donor. The resulting cell population is enriched in stem cells and progenitor cells capable of differentiating along two or more differentiation pathways and is, therefore, useful for a variety of therapeutic applications. In addition, the methods of the present invention are highly efficient, resulting in the expansion of millions of stem cells from a few tissue stem cells.

As described herein, in one embodiment, the methods of the present invention may be used to purify and expand cardiac stem cells and cardiac progenitor cells (CSCs) and prepare a cell population enriched in CSCs having the ability to expand in vitro and in vivo and differentiate along two or more differentiation pathways to produce cardiomyocytes, endothelial cells, smooth muscle cells, or cardiac neural crest cells. However, it is understood that the present invention may also be used to purify and expand stem cells and progenitor cells from other tissues to produce populations enriched in multipotent cells. For example, multipotent stem cells and progenitor cells may be isolated from adult, juvenile, or fetal tissue. In addition, it may be isolated from somatic tissue or embryonic tissue.

As used in the specification and appended claims, unless specified to the contrary, the following terms have the meaning indicated:

A "stem cell" refers to an undifferentiated, multipotent, self-renewing, cell. A stem cell is able to divide and, under appropriate conditions, has self-renewal capability and can include in its progeny daughter cells that can terminally differentiate into any of a variety of different cell types. Hence, the stem cell is "multipotent" because stem cell progeny have multiple differentiation pathways. A stem cell is capable of self maintenance, meaning that with each cell division, one daughter cell will also be on average a stem cell.

The non-stem cell progeny of a stem cell are typically referred to as "progenitor" cells, which are capable of giving rise to various cell types within one or more lineages. The term "progenitor cell" refers to an undifferentiated cell derived from a stem cell, and is not itself a stem cell. Some progenitor cells can produce progeny that are capable of differentiating into more than one cell type. A distinguishing feature of a progenitor cell is that, unlike a stem cell, it does not exhibit self maintenance, and typically is thought to be committed to a particular path of differentiation and will, under appropriate conditions, eventually differentiate along this pathway.

The term "precursor cells" refers to the progeny of stem cells, and thus includes both progenitor cells and daughter stem cells.

Stem cells and progenitor cells derived from a particular tissue are referred to herein by reference to the tissue from which they were obtained. For example, stem cells and progenitor cells obtained from cardiac tissue are referred to as "cardiac stem cells" and "cardiac progenitor cells," respectively.

A "clonogenic population" refers to a population of cells derived from the same stem cell. A clonogenic population may include stem cells, progenitor cells, precursor cells, and differentiated cells, or any combination thereof.

The term "purified" or "enriched" indicates that the cells are removed from their normal tissue environment and are present at a higher concentration as compared to the normal tissue environment. Accordingly, a "purified" or "enriched" cell population may further include cell types in addition to stem cells and progenitor cells and may include additional tissue components, and the term "purified" or "enriched" does not necessarily indicate the presence of only stem cells and progenitor cells.

A. Methods of Purifying and Expanding Stem Cells

The present invention provides methods of purifying from mammalian tissue, multipotent cells (e.g., stem cells and progenitor cells) that retain the ability to proliferate and differentiate along two or more pathways. These methods do not require harsh enzymatic treatment of the tissue, which can result in the loss of certain cell surface proteins and markers and an associated decreased ability to proliferate and differentiate. In addition, the present invention provides methods of culturing, expanding, and cloning stem cells to produce a population highly enriched in stem cells and progenitor cells. These populations are substantially free of contaminating cell types, such as fibroblasts, which can result in scar formation and can compete with stem cells and progenitor cells in repopulating an injured tissue. Accordingly, the present invention provides highly efficient methods of generating a population of multipotent stem cells from a small number of tissue stem cells. These methods are particularly useful in generating therapeutic amounts of multipotent stem cells from the small number of stem cells available in certain tissues, such as heart tissue.

In one embodiment, the present invention provides a method of purifying stem cells or progenitor cells from a tissue sample, comprising culturing a mammalian tissue sample comprising stem cells or progenitor cells in vitro under conditions suitable for cell growth and for a time sufficient to permit cell adherence to the culture dish, obtaining non-adherent and weakly adherent cells present in the culture medium or loosely attached above the layer of adherent cells, and isolating from the obtained cells those cells expressing a surface or internal marker of stem or progenitor cells.

In another embodiment, the present invention further provides a method of expanding purified stem cells or progenitor cells in the absence of support cells or feeder cells, such as fibroblasts. This method comprises culturing the purified stem cells and/or progenitor cells in cell growth medium supplemented with conditioned medium, purified growth factors, or both, in the absence of exogenously supplied support or feeder cells, such as fibroblasts. The method may be used to clone individual stem cells by culturing purified stem cells in isolating, e.g., one cell or one cell clone per culture well, during expansion, thereby producing clonogenic populations of stem cells.

The purification and expansion methods described above may be used in combination to obtain a population enriched in stem cells, progenitor cells, or both stem cells and progenitor cells. Accordingly, in one embodiment, the present invention provides a method of preparing a population enriched in mammalian stem cells, progenitor cells or both stem cells and progenitor cells, comprising culturing a mammalian tissue sample comprising stem cells or progenitor cells in vitro under conditions suitable for cell growth and for a time sufficient to permit cell adherence to the culture dish, obtaining non-adherent and weakly adherent cells present in the culture medium or loosely attached above the layer of adherent cells, isolating from the obtained cells those cells expressing a surface or internal marker of stem or progenitor cells, culturing and culturing the isolated cells in cell growth medium supplemented with conditioned medium, purified growth factors or both conditioned medium and purified growth factors. The method may be used to prepare a clonogenic population of stem cells by culturing the isolated cells individually, e.g., one cell or one cell clone per culture well. Thus, in one embodiment, the population is a clonogenic population derived from a single tissue-derived stem cell.

In one embodiment, the present invention provides a method of purifying stem cells, progenitor cells, or both stem cells and progenitor cells and a related method of preparing a cell population enriched in stem cells, progenitor cells or both stem cells and progenitor cells, comprising: (1) culturing a tissue sample; (2) obtaining cells that migrate above the layer of adherent cells during culture; (3) cloning one or more cells that migrated above the adherent cells to produce clonogenic populations; and (4) isolating stem cells or progenitor cells from one or more clonogenic populations by cell sorting using one or more cell surface markers or internal markers of stem cells or progenitor cells. This method may further include identifying one or more clonogenic populations having a desired phenotype, such as, e.g., growth or expression of stem cell markers or markers of differentiation down a desired pathway. Markers listed in Table 1 may be used for this purpose. In certain embodiments, the desired phenotype is the expression of one or more genes associated with a desired differentiation pathway or cell type, e.g., a cardiac cell.

In one embodiment, the present invention includes a method of preparing an isolated cell population enriched in stem cells, progenitor cells or both stem cells and progenitor cells, comprising a three step procedure. The first step includes culturing a tissue sample obtained from an animal, such as a mammal or human patient or donor. The second step includes clonegenic screening, which can be performed by: obtaining cells that migrate above adherent fibroblasts during culturing; dispersing a single obtained cell or a single obtained cell clone per well for clonegenic screening; screening to identify clones having a desired phenotype; and culturing one or more clones to produce one or more clonogenic populations. Screening to identify clones having a desired phenotype may be performed, e.g., by sampling a few cells from one or more clonogenic populations and staining the cytoplasm with one or more antibodies and markers associated with a desired cell type. For example, when cardiac stem cells are desired, clones having the desired phenotype may express one or more stem cells markers, as well as or more markers of cardiac tissue, such as, e.g., GATA4, Nkx2.5, myosin, actin, and troponin. Selected clones may then be cultured to increase their number. The third step includes cell sorting using one or more cell surface or internal markers of stem cells, progenitor cells, or both stem cells and progenitor cells; and culturing the isolated stem cells or progenitor cells in conditioned media in the absence of feeder cells; thereby obtaining an isolated cell population enriched in tissue specific stem cells, tissue specific progenitor cells, or tissue specific stem cells and tissue specific progenitor cells. An exemplary method according to this embodiment is shown in FIG. 6.

In particular embodiments, preferred clonogenic population for further expansion are identified based upon their having one or more desirable characteristics, such as, e.g., ability to proliferate; formation of foci or cardiospheres; or expression of one or more stem cell or progenitor cell markers, or one or more markers of differentiation down a desired pathway. In certain embodiment, clonogenic populations are screened for a desired characteristic using high throughput methods. Screening may be performed using a variety of techniques available. For example, screening for cytoplasmic or nucleic markers may be performed by immunocytochemistry-based assays or polymerase chain reaction (PCR)-based assays, such as reverse transcriptase-PCR (RT-PCR), using antibodies or oligonucleotides that bind to a polypeptide or gene more highly expressed in cells having the desired phenotype as compared to other cells.

In certain embodiments, clonogenic populations are expanded prior to cell sorting, by culturing the cells in suitable cell growth medium, preferably in the absence of a feeder layer, and, in certain embodiments, in the presence of conditioned media.

In particular embodiments, cell sorting to purify stem cells, progenitor cells or both stem cells and progenitor cells is performed using an agent that binds one or more cell surface or an internal markers of a particular subpopulation of stem cells, progenitor cells, or both stem cells and progenitor cells, e.g., those that express one or more markers associated with differentiation down a particular pathway, in order to obtain a subpopulation of stem cells, progenitor cells, or both stem cells and progenitor cells.

Purified stem cells and progenitor cells, and cell populations comprising the same, may be expanded in number by culturing the isolated stem cells and progenitor cells in conditioned media in the absence of feeder cells prior to use.

Thus, in one particular embodiment, the present invention includes a method of preparing a cell population enriched in stem cells and/or progenitor cells, comprising: culturing a tissue sample following transient enzymatic treatment to facilitate the release of stem cells and progenitor cells; obtaining cells that migrate above adherent cells during said culturing; cloning one or more cells obtained to produce one or more clonogenic populations, by culturing the cells obtained at a one cell or one cell clone per well ratio; identifying a clonogenic population produced that proliferates and/or expresses one or more selected stem cell or differentiation markers; culturing the identified clonogenic population; isolating stem cells and progenitor cells from the cultured clonogenic population by cell sorting using one or more cell surface (or internal) markers of stem cells and/or progenitor cells; and culturing the isolated stem cells and/or progenitor cells in conditioned media in the absence of feeder cells.

Certain steps of the methods of the present invention, including obtaining tissue samples and culturing cells, may be performed using procedures and reagents known and available in the art.

The methods of the present invention, therefore, provide a variety of advantages over the prior art. First, the purified stem cells and progenitor cells are not subjected to enzymatic treatment. When enzymatic treatment is performed, only the tissue sample is transiently treated with enzymes. Second, isolated purified stem cells and progenitor cells are expanded in the absence of support or feeder cells, so such cells do not contaminate the resulting purified cell population. Third, the methods of the present invention, in certain embodiments, include the cloning of individual stem cells, which allows the selection of clonogenic populations having desired attributes, such as, e.g., expression of specific cell markers, including surface markers present on desired subpopulations of stem cells and progenitor cells and robust cell growth, and cytoplasmic markers such as myosin, nucleic makers and transcription factors. Selection of clones having a desired attribute may be performed by high throughput methods, which allows the rapid screening of a large number of clones. Fourth, the final sorting and purification of the stem cells and progenitor cells based upon expression of a stem cell or progenitor cell marker (and optionally a differentiation marker) may be adapted to purify subpopulations of stem cells having a desired phenotype or expressing a marker that indicates it will differentiate down a desired pathway.

The enriched mammalian stem cell populations of the present invention have a variety of uses, including both autologous and allogeneic therapeutic uses. Accordingly, tissue samples may be obtained from patients to be treated with the purified stem cells or donors. Tissue samples may be obtained from any animal, including, e.g., humans, primates, and domesticated animals and livestock. In preferred embodiments, tissue samples are obtained from mammals. Tissues may include any tissue comprising stem cells, including, e.g., cardiac tissue, adipose tissue, bone marrow, gastrointestinal tissue, epidermal tissue, hepatic tissue, neural tissue, skin tissue, liver tissue, or umbilical cord tissue. In related embodiments, tissue may be ectodermal, mesodermal, or endodermal in origin. Typically, the tissue source is selected based upon the anticipated use; e.g., if the tissue sample is being used to purify stem cells for treatment of a cardiac disease or injury, it will typically be obtained from cardiac tissue. However, it is understood that a tissue sample may be obtained from a tissue type different than the tissue to be treated, so long as the stem cells obtained from such tissue have the capacity to differentiate into a cell type appropriate for treating the diseases or injured tissue.

A tissue sample may be isolated from a patient or donor by any means available in the art. In one embodiment, the tissue sample is a primary tissue explant. In certain embodiments, tissue is isolated by surgical removal or withdrawal using a needle and syringe, e.g., a needle biopsy. A variety of additional procedures are described in U.S. Pat. Nos. 6,020,196 and 5,744,360. Furthermore, tissue may be isolated from any suitable location on an animal, depending upon the type of tissue being isolated. Cardiac tissue may be obtained, e.g., from the myocardium or a coronary blood vessel. Adipose tissue may be isolated from locations including, e.g., the tail head, the omentum or other abdominal location, the stomach, hips or thighs. Umbilical cord matrix cells are typically isolated from the matrix of the umbilical cord, including Wharton's jelly. In one embodiment, cardiac tissue is obtained as described (reference 10).

Tissue samples may be placed into culture without further processing, or they may be processed to release cells from other tissue components by any of a variety of different means or combinations thereof. In many embodiments, tissue is physically processed, e.g., by cutting or mincing a tissue sample into smaller pieces. Cutting may be performed by any means available, including, e.g., the use of scissors, scalpels, razor blades, needles, and other sharp instruments.

In certain embodiments, tissue is processed by exposure to an enzyme preparation that facilitates the release of cells from other tissue components. Examples of such enzymes include matrix metalloproteinases, clostripain, trypsin-like, pepsin-like, neutral protease-type and collagenases. Suitable proteolytic enzymes are described in U.S. Pat. Nos. 5,079,160; 6,589,728; 5,422,261; 5,424,208; and 5,322,790. In one embodiment, the enzyme preparation is a collagenase preparation or comprises collagenase. In related embodiments, the enzyme preparation comprises one or more of trypsin-like, pepsin-like, clostripain, and neutral protease-type enzymes. For example, one suitable enzyme preparation comprises a mixture of 0.2% trypsin and 0.1% collagenase IV.

Stem cells and progenitor cells are purified from other tissue components after or concurrent with the processing of a tissue sample. In one embodiment, stem cells and progenitor cells are purified from other cells and tissue components after the tissue sample has been cultured under conditions suitable for cell growth and for a time sufficient to allow cells to adhere to the culture dish. In certain embodiments, purification of cells comprises obtaining cells that migrate from the tissue sample during culture and are present in the culture media or loosely adhered to the adherent fibroblast layer. In certain embodiment, these cells are small, phase-bright cells. These cells may be obtained by routine methods, such as removing and centrifuging the media to pellet cells therein, and washing the cells remaining in the culture dish with a solution such as phosphate-buffered saline (PBS) or D-Hanks to remove those cells loosely attached to the adherent cell layer. This wash solution may then also be centrifuged to obtain cells.

Tissue samples may be cultured in any of a variety of culture media capable of supporting cell viability, growth and/or attachment, such as serum-supplemented DMEM. In one embodiment, explant media (Iscove's Modified Dulbecco's IMDM with 10% fetal calf serum (FBS), 100 U/ml penicillin G, 100 ug/ml streptomycin, 2 mmol/L L-glutamine, and 0.1 mmol/L 2-mercaptoethanol) is used. Tissue samples are cultured under standard environmental conditions such as 37° C. and 5% $CO_2$. Tissue samples are cultured for a time sufficient for adherent cells to adhere and stem cells to migrate above the adherent cell layer, which may be, e.g., approximately one week, two weeks, or three weeks. Generally, the age of donor tissue determines the time for culture: the older the tissue, the longer the time it takes for the stem cells to migrate out from the explant.

In certain other embodiments, purification of stem cells and progenitor cells may further comprise separating cells from certain insoluble tissue components, including residual tissue material, such as lipids. Cells may be separated from other tissue components by any means known and available in the art, including, e.g., the use of density gradients, centrifugation, and filtration or combinations thereof. Examples of specific methods of purifying cells are known and described in the art, e.g., in U.S. Pat. No. 6,777,231. In certain embodiments, negative separation methods are employed to remove one or more particular types of cells.

In order to enrich for stem cells and/or progenitor cells, the cells purified from the tissue sample are sorted using one or more reagents that bind to cell surface (or internal) markers indicative of stem cells (or progenitor) cells ("cell surface stem (or progenitor) cell markers"). For example, the present invention contemplates any suitable method of employing monoclonal antibodies to separate stem cells or progenitor cells from other cells recovered from the tissue sample. These methods include, e.g., contacting a cell suspension comprising the cells purified from the tissue sample with one or a combination of monoclonal antibodies that recognize an epitope on stem or progenitor cells; and separating and recovering from the cell suspension the cells bound by the monoclonal antibodies. In one embodiment, cells are selected using antibodies bound to magnetic beads and a magnetic cell sorter device. In one embodiment, cells are selected by fluorescence activated cell sorting (FACS) using fluorescently labeled antibodies. In other embodiments, the monoclonal antibodies may be linked to a solid-phase and utilized to capture mesenchymal stem cells from tissue samples. The bound cells may then be separated from the solid phase by known methods depending on the nature of the antibody and solid phase. Examples of monoclonal antibody-based systems appropriate for preparing the desired cell population include magnetic cell sorting, FACS, magnetic bead/paramagnetic particle column utilizing antibodies for either positive or negative selection; separation based on biotin or streptavidin affinity; and high speed flow cytometric sorting of immunofluorescent-stained stem cells mixed in a suspension of other cells.

Exemplary cell surface or internal markers of stem cells or progenitor cells include, but are not limited to, Sca-1, c-Kit, ATP-binding cassette transporter, B1-3, Flk-1, CD31, CD34, Isl1, GATA4, nkx2.5, and the markers listed in Table 1.

Monoclonal antibodies that specifically bind to stem or progenitor cells are known and available in the art, and many of these are specific for stem or progenitor cells derived from one or more tissue types. For example, Sca-1 is a surface marker of cardiac and other somatic stem cells. In certain embodiments, stem cells, e.g., cardiac stem cells, are isolated using antibodies specific for Sca-1. Anti-Sca-1 microbeads suitable for such use are commercially available from Miltenyi Biotec. Cardiac stem cells express additional cell surface markers that can be used in their isolating, including, e.g., c-kit, Flk, CD31, sca-1, ABCG2, CD133 and Stro-1. Other cell surface markers that may be used according to the present invention include, but are not limited to, those cell surface markers listed in Table 1 as being associated with stem or progenitor cells, which may be used to select cells of their associated cell types.

TABLE 1

Exemplary markers and their associated cell types (from The National Institutes of Health resource for stem cell research)

| Marker Name | Cell Type | Significance |
|---|---|---|
| Blood Vessel | | |
| Fetal liver kinase-1 (Flk1) | Endothelial | Cell-surface receptor protein that identifies endothelial cell progenitor; marker of cell-cell contacts |
| Smooth muscle cell-specific myosin heavy chain | Smooth muscle | Identifies smooth muscle cells in the wall of blood vessels |
| Vascular endothelial cell cadherin | Smooth muscle | Identifies smooth muscle cells in the wall of blood vessels |
| Bone | | |
| Bone-specific alkaline phosphatase (BAP) | Osteoblast | Enzyme expressed in osteoblast; activity indicates bone formation |
| Hydroxyapatite | Osteoblast | Minerlized bone matrix that provides structural integrity; marker of bone formation |
| Osteocalcin (OC) | Osteoblast | Mineral-binding protein uniquely synthesized by osteoblast; marker of bone formation |
| Bone Marrow and Blood | | |
| Bone morphogenetic protein receptor (BMPR) | Mesenchymal stem and progenitor cells | Important for the differentiation of committed mesenchymal cell types from mesenchymal stem and progenitor cells; BMPR identifies early mesenchymal lineages (stem and progenitor cells) |
| CD4 and CD8 | White blood cell (WBC) | Cell-surface protein markers specific for mature T lymphocyte (WBC subtype) |
| CD34 | Hematopoietic stem cell (HSC), satellite, endothelial progenitor | Cell-surface protein on bone marrow cell, indicative of a HSC and endothelial progenitor; CD34 also identifies muscle satellite, a muscle stem cell |
| $CD34^+Sca1^+Lin^-$ profile | Mesencyhmal stem cell (MSC) | Identifies MSCs, which can differentiate into adipocyte, osteocyte, chondrocyte, and myocyte |
| CD38 | Absent on HSC Present on WBC lineages | Cell-surface molecule that identifies WBC lineages. Selection of $CD34^+/CD38^-$ cells allows for purification of HSC populations |
| CD44 | Mesenchymal | A type of cell-adhesion molecule used to identify specific types of mesenchymal cells |

TABLE 1-continued

Exemplary markers and their associated cell types (from The National Institutes of Health resource for stem cell research)

| Marker Name | Cell Type | Significance |
| --- | --- | --- |
| c-Kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Colony-forming unit (CFU) | HSC, MSC progenitor | CFU assay detects the ability of a single stem cell or progenitor cell to give rise to one or more cell lineages, such as red blood cell (RBC) and/or white blood cell (WBC) lineages |
| Fibroblast colony-forming unit (CFU-F) | Bone marrow fibroblast | An individual bone marrow cell that has given rise to a colony of multipotent fibroblastic cells; such identified cells are precursors of differentiated mesenchymal lineages |
| Hoechst dye | Absent on HSC | Fluorescent dye that binds DNA; HSC extrudes the dye and stains lightly compared with other cell types |
| Leukocyte common antigen (CD45) | WBC | Cell-surface protein on WBC progenitor |
| Lineage surface antigen (Lin) | HSC, MSC Differentiated RBC and WBC lineages | Thirteen to 14 different cell-surface proteins that are markers of mature blood cell lineages; detection of Lin-negative cells assists in the purification of HSC and hematopoietic progenitor populations |
| Mac-1 | WBC | Cell-surface protein specific for mature granulocyte and macrophage (WBC subtypes) |
| Muc-18 (CD146) | Bone marrow fibroblasts, endothelial | Cell-surface protein (immunoglobulin superfamily) found on bone marrow fibroblasts, which may be important in hematopoiesis; a subpopulation of Muc-18+ cells are mesenchymal precursors |
| Stem cell antigen (Sca-1) | HSC, MSC | Cell-surface protein on bone marrow (BM) cell, indicative of HSC and MSC Bone Marrow and Blood cont. |
| Stro-1 antigen | Stromal (mesenchymal) precursor cells, hematopoietic cells | Cell-surface glycoprotein on subsets of bone marrow stromal (mesenchymal) cells; selection of Stro-1+ cells assists in isolating mesenchymal precursor cells, which are multipotent cells that give rise to adipocytes, osteocytes, smooth myocytes, fibroblasts, chondrocytes, and blood cells |
| Thy-1 | HSC, MSC | Cell-surface protein; negative or low detection is suggestive of HSC |
| Cartilage | | |
| Collagen types II and IV | Chondrocyte | Structural proteins produced specifically by chondrocyte |
| Keratin | Keratinocyte | Principal protein of skin; identifies differentiated keratinocyte |
| Sulfated proteoglycan | Chondrocyte | Molecule found in connective tissues; synthesized by chondrocyte |
| Fat | | |
| Adipocyte lipid-binding protein (ALBP) | Adipocyte | Lipid-binding protein located specifically in adipocyte |
| Fatty acid transporter (FAT) | Adipocyte | Transport molecule located specifically in adipocyte |
| Adipocyte lipid-binding protein (ALBP) | Adipocyte | Lipid-binding protein located specifically in adipocyte |
| Liver | | |
| Albumin | Hepatocyte | Principal protein produced by the liver; indicates functioning of maturing and fully differentiated hepatocytes |
| B-1 integrin | Hepatocyte | Cell-adhesion molecule important in cell-cell interactions; marker expressed during development of liver |

TABLE 1-continued

Exemplary markers and their associated cell types (from The National Institutes of Health resource for stem cell research)

| Marker Name | Cell Type | Significance |
|---|---|---|
| Nervous System | | |
| CD133 | Neural stem cells, HSC | Cell-surface protein that identifies neural stem cell, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |
| Pancreas | | |
| Cytokeratin 19 (CK19) | Pancreatic epithelium | CK19 identifies specific pancreatic epithelial cells that are progenitors for islet cells and ductal cells |
| Glucagon | Pancreatic islet | Expressed by alpha-islet cell of pancreas |
| Insulin | Pancreatic islet | Expressed by beta-islet cell of pancreas Pancreas |
| Insulin-promoting factor-1 (PDX-1) | Pancreatic islet | Transcription factor expressed by beta-islet cell of pancreas |
| Nestin | Pancreatic progenitor | Structural filament protein indicative of progenitor cell lines including pancreatic |
| Pancreatic polypeptide | Pancreatic islet | Expressed by gamma-islet cell of pancreas |
| Somatostatin | Pancreatic islet | Expressed by delta-islet cell of pancreas |
| Pluripotent Stem Cells | | |
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation Pluripotent Stem Cells |
| Bone morphogenetic protein-4 | Mesoderm | Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |

TABLE 1-continued

Exemplary markers and their associated cell types (from The National Institutes of Health resource for stem cell research)

| Marker Name | Cell Type | Significance |
| --- | --- | --- |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Oct-4 | ES, EC | Transcription factor unique to PSCs; essential for establishment and maintenance of undifferentiated PSCs |
| Pax6 | Ectoderm | Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |
| Skeletal Muscle/Cardiac/Smooth Muscle | | |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte |

According to the methods of the present invention, the purified stem or progenitor cells may be expanded and/or cloned in tissue culture. The present invention provides methods of expanding and cloning purified stem cells in culture in the absence of support cells, such as fibroblasts.

In one embodiment, purified stem or progenitor cells, e.g., those obtained after cell sorting using a stem or progenitor cell specific antibody, are cultured in cell growth medium. A variety of media suitable for cell growth are known in the art. Such media typically contain fetal bovine or fetal calf serum at 5%, 10%, 15%, or 20%, L-glutamine, and nonessential amino acids.

In certain embodiments, purified stem or progenitor cells are cultured in cell growth medium supplemented with an additional active agent, such as fibroblast growth factor, heregulin, IGFD-1, activin A, SB203580, or BIO. For example, in one embodiment, the medium used is cell growth medium (CGM; DMEM/F12, 10% fetal bovine serum, 200 mmol/L L-glutamine, 0.1 mmol/L β-mercaptoethanol, 1% nonessential amino acids, 1000 units/ml LIF, 0.1 unit/ml thrombin and 5 ng/ml fibroblast growth factor).

In certain embodiments, the purified stem or progenitor cells are cultured in conditioned growth media. Conditioned growth media may be prepared, for example, by exposing media for at least 24 hours, preferably 48 hours, to a fibroblast culture, thereby allowing it to dissolve and take up paracrine factors from the fibroblasts.

In certain embodiments, the purified stem or progenitor cells may be expanded in cell growth media supplemented with conditioned growth media, e.g., to achieve a final ratio of 1:1, 1:2, 1:3, 1:4, or 1:5 (cell growth media:conditioned growth media).

In certain embodiments, the purified stem or progenitor cells may be expanded in cell growth media supplemented with both conditioned growth media and an additional active agent, such as bFGF (e.g., at 5 ng/ml), heregulin, IGF-1, activin A, SB203580, or BIO. In one particular embodiment, purified stem cells are expanded or cloned in conditioned CGM (CCGM) mixed with CGM at a 3:1 ratio and supplemented with additional bFGF at 5 ng/ml.

To produce clonogenic populations of stem cells and progenitor cells, purified cells may be plated a one cell or one cell clone per well ratio. In certain embodiment, cells are plated in plates, e.g., multiwell plates, precoated with basement membrane or extracellular matrix components, such as the solubulized basement membrane preparation, BD Matrigel™ (BD Biosciences).

When culturing cardiac tissue explants, cardiac fibroblasts, which are the majority cell population in the normal adult heart (reference 19), tend to spread in sheet-like extensions. They provide a feeder layer for cardiac stem cell proliferation and migration from explants (reference 10). Considering that the soluble paracrine factors produced by cardiac fibroblasts may be important for the proliferation of cardiac stem cells, the present invention provides for the use of cardiac fibroblast-free conditioned medium to support cardiac stem cell growth. For example, cell culture medium may be conditioned by exposing it for 48 hours to fibroblast culture to extract paracrine factors from fibroblasts. In addition, purified stem cells and progenitor cells may be grown on BD-Matrigel™, which provides the required adhesion for survival and growth of cardiac stem cell, because it contains mostly lamanin, collagen IV, and heparin sulfate proteoglycan. As demonstrated in the accompanying examples, stem cells and progenitor cells could be expanded using the fibroblast-free conditioned cell medium and BD-Matrigel™-coated plates, while avoiding the contamination of fibroblasts.

As described above, the methods of the present invention may be used to prepare a cell population enriched in multipotent stem cells and progenitor cells. Thus, in various embodiments, the purified cell population comprises at least 75%, at least 80%, at least 85%, at least 90%, at least 95%, at least 96%, at least 97%, at least 98%, at least 99%, or 100% stem cells and progenitor cells, as indicated by the presence of one or more stem cell markers, such as Sca-1.

The cell populations prepared according to the methods of the present invention comprise multipotent cells capable of undergoing differentiation into two or more specialized cell types. For example, purified CSCs are capable of differentiating into two or more of myocytes, endothelial cells, smooth muscle cells, and cardiac neural crest cells. In particular embodiments, at least 75%, at least 80%, at least 85%, at least 80%, at least 95%, at least 96%, at least 97%, at least 98%, at least 99%, or 100% of the cells in the cell population have the capacity to undergo differentiation into two or more specialized cell types. Cardiac stem cells give rise to a variety of cells, including, e.g., myocytes, endothelial cells, smooth muscle cells, and cardiac neural crest cells. Hematopoietic stem cells give rise to all types of blood cells, including red blood cells, B lymphocytes, T lymphocytes, natural killer cells, neutrophils, basophils, eosinophils, monocytes, macrophages, and platelets. Bone marrow stromal cells give rise to a variety of cell types: bone cells (osteocytes), cartilage cells (chondrocytes), fat cells (adipocytes), and other kinds of connective tissue cells such as those in tendons. Neural stem cells in the brain give rise to its three major cell types: nerve cells (neurons) and two categories of non-neuronal cells: astrocytes and oligodendrocytes. Epithelial stem cells in the lining of the digestive tract occur in deep crypts and give rise to several cell types: absorptive cells, goblet cells, Paneth cells, and enteroendocrine cells. Skin stem cells occur in the basal layer of the epidermis and at the base of hair follicles. The epidermal stem cells give rise to keratinocytes, which migrate to the surface of the skin and form a protective layer. The follicular stem cells can give rise to both the hair follicle and to the epidermis.

The ability to differentiate may be readily determined by exposing a population of cells to suitable environmental conditions and/or differentiation inducers for a time sufficient to allow differentiation to occur, and then examining the cells for their expression of differentiation markers. Such conditions and differentiation markers are known and available for a wide variety of cell types. For example, a variety of cell surface markers are expressed in different cell types and at different stages of differentiation, including those listed in Table 1. The presence of one or more of these cell surface markers may be determined by routine methods, including, e.g., flow cytometry and PCR-based assays, using antibodies or primers that bind to the markers or encoding nucleic acid sequences. By determining the presence or absence of markers associated with various paths and/or stages of differentiation, the skilled artisan can readily determine the differentiation path and/or stage associated with a particular cell or cell population.

Examples of suitable cardiac differentiation markers include GATA4, Nkx2.5, cTnI, C31, SM-actin, connexin43, and myosin. Examples of adipocyte differentiation markers include C/EBPalpha, PPARgamma, adipsin, leptin, and UCP1. Examples of osteogenic differentiation markers include osteopontin, sialoprotein, osteocalcin, and osteonectin. Examples of chondrogenic differentiation markers include collagen II, and aggrecan. Examples of neural differentiation markers include β-III tublin, Pax6 expression, GFAP, and nestin.

The methods of the present invention are particularly useful in preparing populations of stem cells and progenitor cells derived from tissues containing a relatively small number of stem cells and progenitor cells, such as cardiac tissue. Thus, in one particular embodiment, the present invention provides a method to prepare a population enriched in multipotent CSCs and progenitor cells, comprising purifying endogenous CSCs and progenitor cells from a primary heart tissue explant, isolating CSCs and progenitor cells from fibroblasts by cell sorting with stem cell markers, and culturing the isolated CSCs and progenitor cells. A fibroblast-free culture system is used for the culturing of CSCs and progenitor cells. As described in the following examples, this method yielded 97.6% pure Sca-1+ cells that retained the capacity to form new cardiospheres, indicating that they can renew themselves, and were clonogenic. These cells were further characterized by immunostaining for cardiac-specific transcription factor (GATA4) and were capable of undergoing differentiation both in vitro and in vivo. When systemically injected into mice subjected to a myocardial infarction, the cells gave rise to cardiomyocytes, endothelial cells, and smooth muscle.

Accordingly, the present invention provides methods for the isolation of intact CSCs and CPCs, using antibodies specific for Sca-1. This method avoids the possible enzymatic destruction of functional stem cell markers at cell surface by culturing the Sca-1 cell in a fibroblast-free culture system comprising conditioned medium, which supports the growth of CSCs. The resulting Sca-1+ cells were demonstrated to be functional in vitro and in vivo. After been injected into mice with myocardial ischemia, Sca-1+ cells were detectable in the heart for up to one month after injection, and differentiated to cardiomyocytes, endothelial cells and smooth muscle cells. The methods of the present invention can also be used to isolate other possible types of CSCs, e.g., by isolating cells using antibodies specific for c-kit or ABCG2.

Cells prepared according to the methods of the invention may be used immediately or stored prior to use. The cells may be used without any further culturing, or they may be cultured and/or differentiated prior to use. The cells may be stored temporarily under cool conditions, e.g., under refrigeration, or at approximately 2-10° C., or the cells may be frozen under liquid nitrogen for long term storage. A variety of methods of freezing cells for long term storage and recovery are known in the art and may be used according to the invention, including freezing cells in a medium comprising fetal bovine serum and dimethylsulfoxide (DMSO).

In certain embodiments, cells are differentiated prior to use. Thus, any of the methods described herein may further include differentiating isolated or purified stem cells and progenitor cells. Cells may be induced to differentiate using any method available in the art. Typically, cells are induced to differentiate by contacting them with one or more differentiation agents or factors, which may be chemicals, polypeptides, nucleic acids, or environmental conditions. Examples of differentiation factors include, but are not limited to, member of the transforming growth factor β superfamily, such as transforming growth factor β, bone morphogenic protein 2 or 4, or activin A; chemical inducers, such as 5-azacytidine and DMSO; compounds that activate developmental signaling pathways, such as Wnt and Notch; and other growth factors, such as VEGF and bFGF.

B. Purified Stem Cells and Methods of Use Thereof

The present invention also provides populations of cells enriched in multipotent stem cells and progenitor cells, e.g., cardiac stem cells and progenitor cells, which are substantially free of or free of contaminating fibroblasts and other cells. These populations are advantageous over previously described populations of purified stem cells and progenitor cells, including those prepared using harsh enzymatic treatment, since they retain cell surface molecules involved in biological activity and retain the ability to differentiate into two or more specialized cell types. In addition, these cell populations do not include fibroblasts, which lead to undesired scar formation when administered to a wound or disease site. In addition, contaminating cells, such as fibroblasts, can proliferate more rapidly than stem cells and compete with stem cells in repopulating a tissue site when administered therapeutically. Accordingly, the cell populations of the present invention include two desirable features not previously present in populations of stem cells and progenitor cells prepared using a mammalian tissue sample: (1) functional activity characterized by the ability to differentiate into two or more different specialized cell types, e.g., smooth muscle cells, myocytes, endothelial cells, or cardiac neural crest cells; and (2) free of contaminating fibroblasts and other cell types.

Thus, in various embodiments, a purified cell population of the present invention comprises at least 75%, at least 80%, at least 85%, at least 90%, at least 95%, at least 96%, at least 97%, at least 98%, at least 99%, or 100% stem cells and progenitor cells, as indicated by the presence of one or more stem cell markers, such as Sca-1.

In particular embodiments, at least 75%, at least 80%, at least 85%, at least 90%, at least 95%, at least 96%, at least 97%, at least 98%, at least 99%, or 100% of the cells in a cell population of the present invention have the capacity to undergo differentiation into two or more specialized cell types.

In another embodiment, a cell population of the present invention comprises CSCs and CPCs, wherein at least 75%, at least 80%, at least 85%, at least 90%, at least 95%, at least 96%, at least 97%, at least 98%, at least 99%, or 100% of the cells in the cell population have the capacity to form cardiospheres.

In another embodiment, a cell population of the present invention comprises CSCs and CPCs, wherein at least 75%, at least 80%, at least 85%, at least 90%, at least 95%, at least 96%, at least 97%, at least 98%, at least 99%, or 100% of the cells in the cell population express GATA4.

In one specific embodiment, a cell population of the present invention comprises CSCs and CPCs, wherein at least 95% of the cells are Sca-1$^+$CD45$^-$. In particular embodiments, at least 75%, at least, 85%, or at least 95% of the cells are capable of differentiating into a cardiacmyocyte, endothelial cell, smooth muscle cell, or cardiac neural crest cell.

As shown in the accompanying examples, the present invention provides cell populations enriched in Sca-1+ cells lacking the hematopoietic stem cell markers CD45, and expressing GATA-4, which is a cardiac transcription factor (references 13 and 21). GATA4 activates the promoters of several cardiac genes, such as myosin light chain, Nkx2.5, troponin T, troponin I, α-MHC, and ANP (reference 9). Sca-1+ cells facilitate the expression of cardiac structure proteins, such as myosin and connexin43. These cells also possess multipotency. After being given intravenously to mice post-MI, these stem cells homed to injured myocardium and differentiated into cardiomyocytes, endothelial cells, and smooth muscle cells in the border zone at four weeks post-transplantation.

In related embodiments, the cell population comprises clonogenic cells, i.e., cells derived from the same stem cell.

In certain embodiments, the purified cell populations of the present invention are present within a composition, e.g., a pharmaceutical composition, adapted for and suitable for delivery to a patient, i.e., physiologically compatible. Accordingly, the present invention includes compositions comprising a stem cell population of the present invention and one or more of buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

In related embodiments, the present invention provides a pharmaceutical composition that comprises the purified cell populations provided herein and a biological compatible carrier or excipient, such as 5-azacytidine, cardiogenol C, or ascorbic acid.

In related embodiments, the purified cell populations are present within a composition adapted for or suitable for freezing or storage. For example, the composition may further comprise fetal bovine serum and/or dimethylsulfoxide (DMSO).

The present invention further provides methods of treating or preventing injuries and diseases or other conditions, comprising providing a cell population of the present invention, i.e., a population enriched in stem cells and progenitor cells, to a patient suffering from said injury, disease or condition. In particular embodiments, the cell population was generated using a tissue sample obtained from the patient being treated (i.e., autologous treatment). In other embodiments, the cell population was obtained from a donor, who may be related or unrelated to the patient (i.e., allogeneic treatment). The donor is usually of the same species as the patient, although it is possible that a donor is a different species (i.e., xenogeneic treatment).

In various embodiments, the stem cell populations and related compositions are used to treat a variety of different diseases, including but not limited to inflammatory diseases, cardiovascular diseases, nervous system diseases, tumors, demyelinating diseases, digestive system diseases, endocrine system diseases, reproductive system diseases, hemic and lymphatic diseases, immunological diseases, mental disorders, musculoskeletal diseases, neuromuscular diseases, metabolic diseases, skin and connective tissue diseases, and urological diseases.

In other embodiments, the purified stem cells and related compositions are used to treat a variety of different wounds, including but not limited to, abrasions, avulsions, blowing wounds, incised wounds, burns, contusions, puncture wounds, surgical wounds and subcutaneous wounds.

In specific embodiments, the present invention provide a methods for treating or preventing cardiovascular diseases and injuries, including but not limited to diseases of the myocardium, abscess, congenital heart deficit, heart valve disease, arrhythmia, left ventricular dilatation, emboli, heart failure, congestive heart failure, subendocardial fibrosis, left or right ventricular hypertrophy, acute myocardial infarct, organizing myocardial infarct, and myocarditis. These methods comprise providing a cell population of the present invention, wherein said cell population is enriched in multipotent CSCs and CPCs, to a patient diagnosed, suspected of having, or being at risk of a cardiovascular disease or injury. In a preferred embodiment, the CSCs and CPCs were isolated from the patient being treated.

In a related embodiment, the present invention includes a method of reconstituting or repopulating dead or injured myocardium in a patient. This method comprises contacting a patient having injured or dead myocardium with a cell population of the present invention, enriched in CSCs and CPCs. In one embodiment, the patient previously suffered a myocardial infarction and/or has been diagnosed with congestive heart failure. As shown in the following examples, Sca-1+ cells extracted and purified by methods of the present invention are multipotent and can be used to reconstitute dead myocardium by differentiating to normal components of adult hearts after being transplanted into ischemia-induced heart of mice.

Myocardial infarction is one of the leading causes of congestive heart failure in the United States, with median survival after onset only 1.7 years in men and 3.2 years in women (reference 16). The irreversible loss of myocytes induced by myocardial infarction leads to a sequence of congestive heart failure. The longstanding dogma of the heart as a terminally differentiated tissue incapable of regeneration has recently been challenged. Investigators from different laboratories have only recently discovered stem cells in the adult heart (references 8, 10-13, 17, and 18). These cells are rare, but might have appropriate regenerative potential for repairing injured hearts. However, myocardial failure is usually irreversible. This may be due to the inadequate numbers of resident cardiac stem cells to replace injured heart issue and the negative environment of ischemic heart for stem cell proliferation and survival.

Although the small number of resident cardiac stem cells may not be sufficient to restore heart function after MI, their presence has raised the possibility of regenerating damaged heart tissue by using them, if they can be expanded and purified in vitro. Oh et al. (reference 9) has reported cardiac Sca-1+ cells lacking hematopoietic stem cell markers CD45, and also lacking transcripts for cardiac structural genes (myosin light chains), but expressing the cardiac transcription factor GATA-4. Matsuura et al. (reference 17) showed that adult cardiac Sca-1+ cells can differentiate into beating cardiomyocytes with multipotency. However, for treatment, the technical difficulties lie in collecting the endogenous stem cells from adult hearts, because they are rare in the heart and enzymatic digestion can destroy the integrity of stem cell markers, which leads to sorted cells losing their potential as stem cells.

The methods of the present invention can be used to isolate and culture large number of CSCs free of contaminating fibroblasts, which is important for clinical applications. Messina et al. (reference 10) recently reported a method to culture cardiospheres from human myocardial biopsies that expressed Sca-1, c-kit, Flk and CD31. Myocytes constitute the majority of cardiac tissue volume, however, fibroblasts dominate in number, and their proliferation is associated with many cardiac pathologies (reference 19). Excluding fibroblasts from cardiac stem cell culture is important, because fibroblasts maintain high proliferative potential and will overgrow cardiac stem cells in cardiosphere. To avoid the contamination of fibroblast, the methods of the present invention combine primary tissue explant with cell sorting to produce large numbers of purified Sca-1+ cells. In certain embodiments, these methods are used to isolate and purify cardiac stem/progenitor cells that migrate from heart explants, not from enzymatically-digested heart. This avoids the direct enzymatic digestion of cardiac stem cells, and maintains the integrity of stem cell marker at the cell surface.

Cell populations and related compositions of the present invention may be provided to a patient by a variety of different means. In certain embodiments, they are provided locally, e.g., to a site of actual or potential injury or disease. In one embodiment, they are provided using a syringe to inject the compositions at a site of possible or actual injury or disease. In other embodiments, they are provided systemically. In one embodiment, they are administered to the bloodstream intravenously or intra-arterially. The particular route of administration will depend, in large part, upon the location and nature of the disease or injury being treated or prevented. Accordingly, the invention includes providing a cell population or composition of the invention via any known and available method or route, including but not limited to oral, parenteral, intravenous, intra-arterial, intranasal, and intramuscular administration.

The development of suitable dosing and treatment regimens for using the cell populations and compositions described herein in a variety of treatment regimens, including e.g., oral, parenteral, intravenous, intranasal, and intramuscular administration and formulation, will again be driven in large part by the disease or injury being treated or prevented and the route of administration. The determination of suitable dosages and treatment regimens may be readily accomplished based upon information generally known in the art and obtained by a physician.

Treatment may comprise a single treatment or multiple treatments. In particular, for preventative purposes, it is contemplated in certain embodiments that purified cell populations of the invention are administered during or immediately following a stress that might potentially cause injury, such as, e.g., myocardial infarction.

The present invention also provides kits useful in the preparation and/or use of the purified cell populations of the present invention, which are enriched in stem cells and progenitor cells. For example, in one embodiment, a kit useful in the preparation of the purified cell populations is provided that comprises an agent that binds a cell surface marker of stem cells or progenitor cells, and conditioned medium. For example, a kit may include: a first container comprising an antibody specific for a stem cell surface marker, wherein said antibody is adapted for isolation or detection, e.g., by being conjugated to a fluorescent marker or magnetic bead; and a second container comprising conditioned medium. In various related embodiments, the kits may further comprise one or more additional reagents useful in the preparation of a cell population of the present invention, such as cell culture medium, BD-Matrigel™ coated cell culture dishes, and enzymes suitable for tissue processing. The kit may also include instructions regarding its use to purify and expand stem cells obtained from a tissue sample. In other embodiments, the kits may further comprise a means for obtaining a tissue sample from a patient or donor, and/or a container to hold the tissue sample obtained.

In another embodiment, a kit for using the purified cell populations (e.g., for reconstituting injured or damaged cardiac tissue) is provided that comprises purified cardiac stem or progenitor cells and a vector suitable for transducing the purified cardiac stem or progenitor cells that comprises a reporter gene (e.g., green fluorescent protein (GFP)) under the control of a cardiac specific promoter (e.g., GATA4 promoter). For example, a kit may include: a first container containing purified cardiac stem or progenitor cells; and a second container containing a vector (e.g., a retroviral vector) that comprises the GFP gene under the control of GATA4 promoter.

Example 1

Isolation and Characterization of Cardiac Stem Cell and Progenitor Cell Populations Populations of Sca-1+ cardiac stem cells were isolated and expanded using a two-stage method involving purification of CSCs from a primary tissue explant and cell enrichment. Mouse heart tissue was cultured as previously described (reference 10) with minor modification. Heart tissues were obtained from male mice (2 month old) with approval of the Institutional Animal Care and Use Committee of University of South Florida. Tissues were minced into small pieces and subjected to enzymatic dissociation with a mixture of 0.2% trypsin and 0.1% collagenase IV (Worthington Biochemical Corp.) in PBS three times for 5 minutes at 37° C. After treatment, the remaining tissue fragments were cultured as explants in explant medium (Iscove's Modified Dulbecco's IMDM with 10% fetal calf serum (FBS), 100 U/mL penicillin G, 100 ug/ml streptomycin, 2 mmol/L L-glutamine, and 0.1 mmoL/L 2-mercaptoethanol) at 37° C. and 5% $CO_2$.

At 2-3 weeks after explanting of minced mouse heart tissue, a layer of fibroblasts covered the culture dish, and round, phase-bright cells with different size migrated from the adherent explants (FIG. 1A). These cells were loosely attached to the fibroblast layer, and were collected periodically by simply washing with D-Hanks, to avoid damaging the integrity of cell surface antigen, and centrifuging (FIG. 1B). The cell suspension was filtered through a 40-μm cell strainer (BD Falcon), and cell numbers were counted. To enrich for cardiac progenitor cells, Sca-1+ cells were sorted from the collected cells by positive selection with anti-Sca-1-microbeads (Miltenyi Biotec) using a magnetic cell sorter device from Miltenyi Biotec.

Newly isolated cardiac Sca-1+ cells were seeded in multi-well plates precoated with Matrigel (BD Biosences) in media designated cell growth medium (CGM) (DMEM/F12, 10% FBS, 200 mmol/L L-glutamine, 0.1 mmol/L β-mercaptoethanol, 1% nonessential amino acids, 1000 units/ml LIF, 0.1 unit/ml thrombin and 5 ng/ml basic fibroblast growth factor (bFGF)). This medium was conditioned by exposing it for 48 hours to fibroblast culture to dissolve paracrine factors from fibroblasts. The conditioned medium (CCGM) was mixed with fresh CGM medium at a 3:1 ratio, sterilized by filtration, and supplemented with additional bFGF at 5 ng/ml.

Contrast microscope examinations showed that Sca-1+ cells were bright, round without fibroblast contamination (FIG. 1C). Some of them proliferated and became 2- to 3-cell aggregates in suspension after 3 to 5 days (FIG. 1C). These aggregates slowly increased in size, and gradually attached to the plate. The adherent cells sprouted new round bright cells at their cell body. After 2 weeks, the Sca-1+ cells formed three-dimensional spheres (FIG. 1D). These results demonstrate that CCGM culture medium can be used to expand Sca-1+ cells from mouse myocardium.

Limiting dilution assays were performed to test whether a single Sca-1+ cell from cardiosphere was able to form a sphere. Sorted Sca-1+ cells were seeded into 96-well plates at 1 cell/well (FIG. 1E). Only wells containing a single cell were observed daily for proliferation. They started to proliferate 3 days after seeding, and a small aggregate developed after 10 days (FIG. 1F). A typical cardiosphere appeared after approximately 3 weeks (FIG. 1G), indicating their capacity for self renewal. Sca-1+ cells maintained sphere-forming capacity in the fibroblast-free CCGM medium, and then they gradually became flattened and stopped proliferating.

Figure 1H:
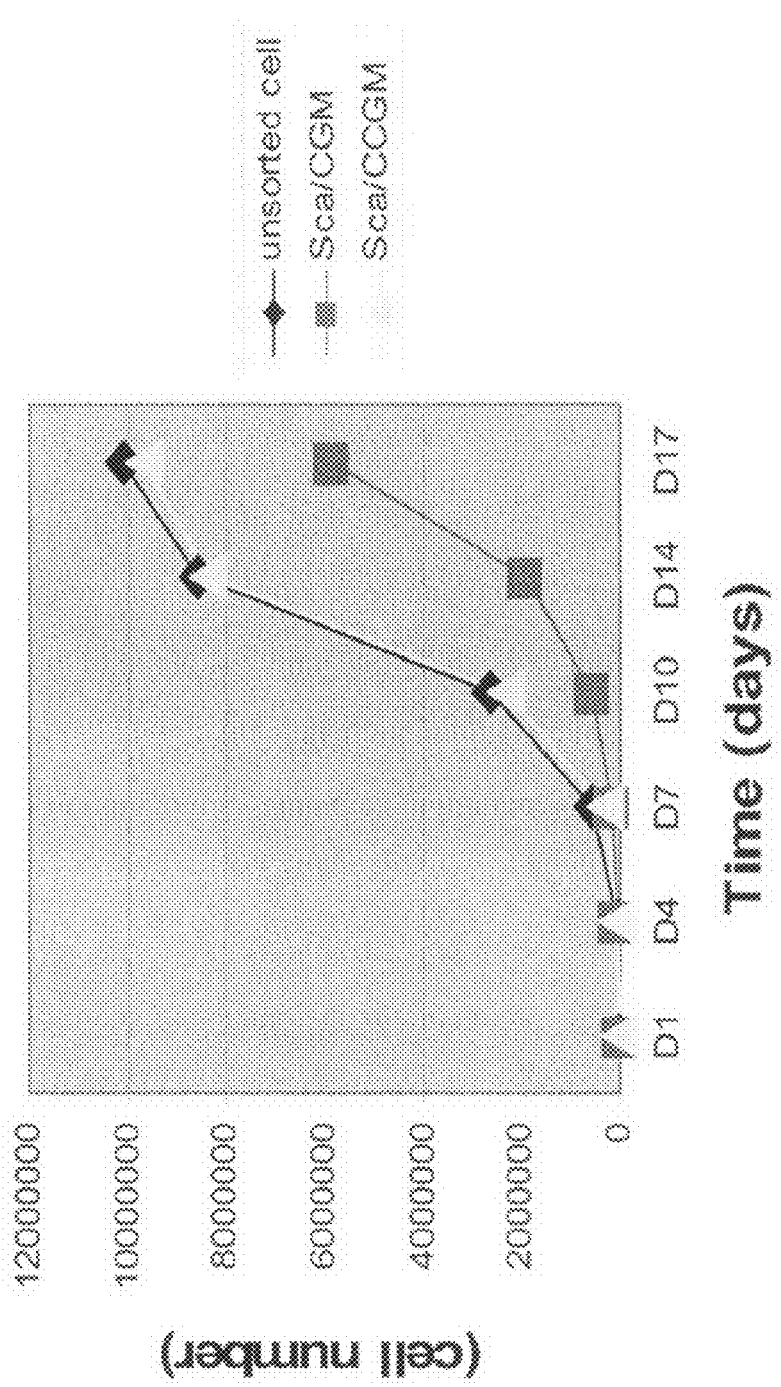
FIG. 1H is a graph depicting cell growth curves of unsorted cardiosphere derived cells, Sca-1+ cells grown in CGM medium, and Sca-1+ cells grown in conditioned CGM (CCGM) medium.

The growth characteristics of the Sca-1+ cells were determined by seeding Sca-1+ cells or unsorted cells in a 100 $cm^2$ dish at the seeding density of $1 \times 10^4$ with CGM medium or conditional CGM medium, which was replaced every 3 days. Cell growth curves were constructed based upon mean values measured by cell counting on day 4, day 7, day 10, day 14 and day 17 (n=4/time point). FIG. 1H shows growth curves demonstrating the effect of CCGM medium on proliferation dynamics of Sca-1+ cell. Compared to CGM medium, it was observed that the absence of cardiac fibroblast inhibited the proliferation of Sca-1+ cells, but the presence of CCGM medium improved the growth of Sca-1+ cell, resulting in cell growth similar to the growth curve of unsorted cardiosphere-derived cells. The CCGM grown Sca-1+ cells were, however, fibroblast-free, unlike the unsorted cells.

Figures 2A, 2B, 2C, 2D, 2E:
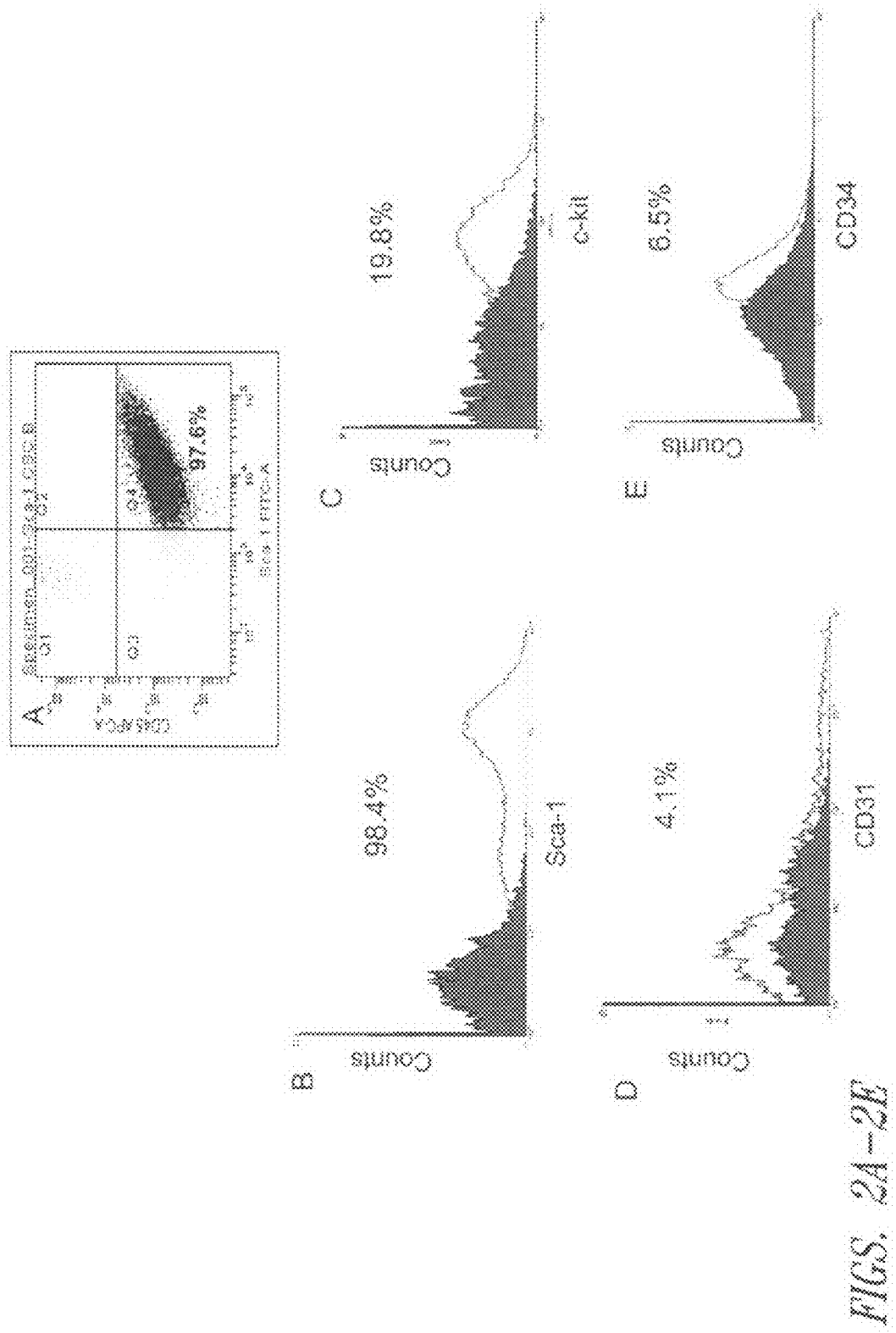
FIGS. 2A-2E graphically depict flow cytometry analysis of Sca-1+ cell populations using antibodies specific for the following cell surface markers: A: Sca-1 and CD45; B: Sca-1; C: c-kit; D: CD31; and E: CD34.

The purity of sorted Sca-1+ cells was demonstrated by flow cytometry. Cultured Sca-1+ cells were blocked with 5% BSA and stained with a panel of antibodies specific for Sca-1, CD45, c-kit, CD31, or CD34 (BD Pharmingen), or isotype controls. Cells were subjected to flow cytometry using BD LSRII flow cytometer and BD FACSDiva™ software. As shown in FIGS. 2A-2B, 97.6% of sorted Sca-1+ cells were Sca-1+CD45⁻. The Sca-1+ cells lacked CD45, a marker of hematopoietic stem cells. Additional marker expression analysis indicated that Sca-1+ cells also expressed another stem cell marker, c-kit (19.8% FIG. 2C). The profile further suggested that a minority of cells expressed CD31 (4.1%; FIG. 2D) or CD34 (6.5%; FIG. 2E) markers.

Phenotypic analysis of newly developing mouse Sca-1+ cells using immunofluorescence confocal microscopy was performed essentially as previously described (reference 3). Cells and tissue were fixed with 4% paraformaldehyde. Primary antibodies specific for ABCG2 (Biotinylated antihuman, 1:100; R&D System), c-kit (Biotinylated antimouse, 1:100; BD Pharmingen), VEGF R2 (Flk-1) (Biotinylated anti-mouse, 1:100; R&D System), GATA4 (goat polyclonal, 1:100; Santa Cruz), Phospho-Histone H3 (Ser10) (rabbit polyclonal, 1:100; Upstate), Myosin (rabbit polyclonal, 1:100; Sigma-Aldrich), and Connexin 43 (mouse monoclonal, 1:100; BD Transduction Lab) were used in immunocytochemistry staining. Isotype-matched antibodies were used as control. These studies indicated that the Sca-1+ cells expressed other stem cell markers, including c-kit (FIG. 3A1-3), ATP-binding cassette transporter (ABCG2), which is a marker for side population stem cells (reference 15) (FIG. 3B1-3), and the endothelial marker, Flk-1 (FIG. 3C1-3).

To further characterize the Sca-1+ cells, the presence of GATA4, a cardiac specific transcription factor, was examined by immunostaining. There were many GATA4-positive cells among the Sca-1+ cells (FIG. 3D1-3) with approximately 55% of the cells expressing detectable levels of GATA4. These results demonstrate that the cells express both a stem cell marker (Sca-1) and a cardiac specific transcription marker (GATA4). This finding is strong evidence that Sca-1+ cells from cardiospheres have entered a differentiation pathway toward a cardiomyocyte phenotype. In addition, some of Sca-1+ cells expressed the serine-10 phosphorylation of histone H3 (FIG. 3E1-3), a marker of mitotic Cdc2 activity and proliferative potential.

Example 2

Figures 4A, 4B, 4C, 4D:
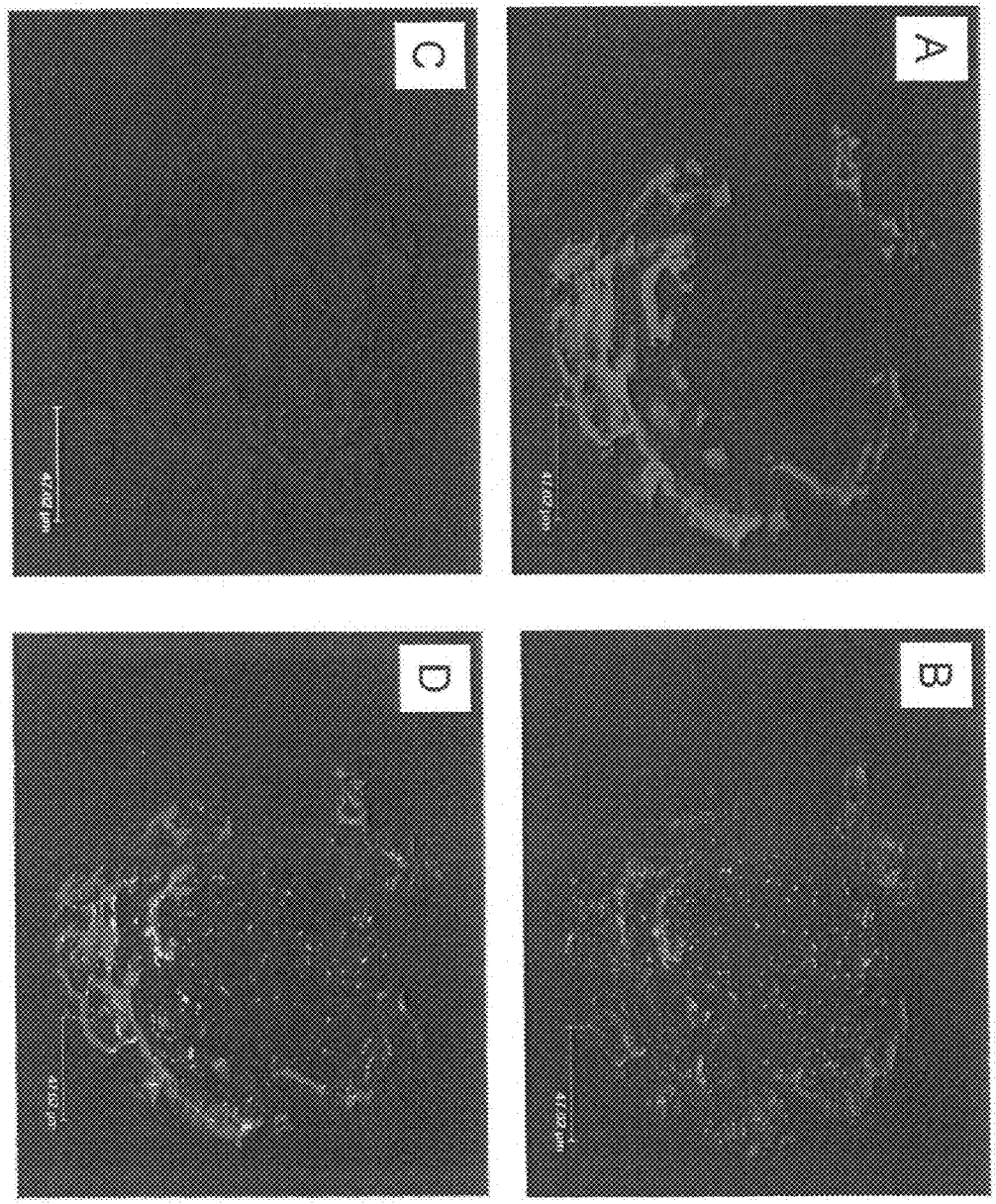
FIGS. 4A-4D provide micrographs showing immunofluorescence staining of an Sca-1+ cell sphere formed in vitro after 2 days of exposure to low serum medium.

In Vitro Differentiation of Cardiac Stem Cell and Progenitor Cell Populations To analyze the spontaneous differentiation of Sca-1+ cell-formed spheres, cardiac Sca-1+ cells isolated as described in Example 1 were exposed to low-serum medium (2% FBS) for 2 days, and assayed for the expression of the cardiomyocyte structure proteins, myosin and connexin43, by immunofluorescent staining. As shown in FIGS. 4A-D, confocal immunofluorescence analysis of a cardiosphere using anti-connexin43 (green) and anti-myosin (red) antibodies revealed spontaneous differentiation present in the peripheral zone of sphere (FIG. 4A arrow). These results suggest that, in an in vitro low serum environment, Sca-1+ cell-formed spheres are capable of differentiating into cardiomyocytes.

Example 3

Figure 5A:
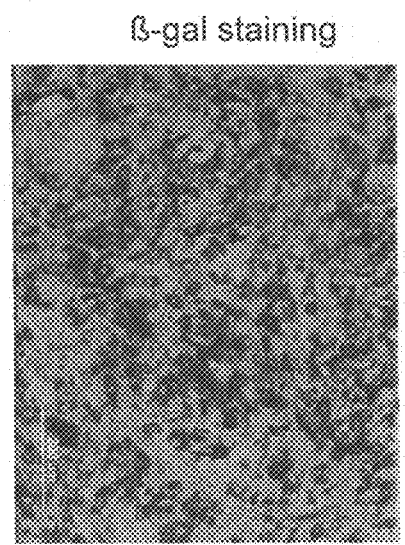
FIGS. 5A-5D provide micrographs demonstrating engraftment and multilineage differentiation of graft Sca-1+ cells in ischemic myocardium.

In Vivo Differentiation of Cardiac Stem Cell and Progenitor Cell Populations The ability of Sca-1+ cells to differentiate and reconstitute the myocardium in vivo was examined in mice treated with LacZ-labeled Sca-1+ cells. To track the cells after transplantation in the heart, Sca-1+ cells were genetically engineered to express the LacZ reporter gene. Sca-1+ cells were transduced with the retroviral reporter vector packaged from pCL-MFG-LacZ plasmid (Imgenex). Retronectin dishes (Takara Bio Inc.) were used to increase the transduction ratio of retrovirus. The transduction efficiency was evaluated by LacZ detection kit for cells (InvivoGen). Transduction was measured at greater than 90% efficiency by β-gal staining (FIG. 5A).

Male C57/BL6 mice (4 month old) were anesthetized with sodium pentobarbital (40 mg/kg, i.p.) and mechanically ventilated. Myocardial infarction was induced via ligation of the left anterior descending coronary artery 2 mm from the tip of the normally positioned left auricle as described previously (reference 2) (n=8). 10 min after ligation, a 200 µl solution containing $1 \times 10_6$ Sca-1+ cells in PBS was intravenously injected into the mice through right jugular vein. Hearts were harvested from the mice 1 month after cell injection.

The hearts were embedded in OCT compound and sectioned at 5 µm. Incorporated LacZ-labeled cells were detected by the FITC conjugated anti-LacZ antibody (1:500, Abcam). An anti-cTnI (1:100, Santa Cruz), anti-CD31 biotin antibody (1:100, BD PharMingen) and anti-SMA (1:100, Zymed Lab) were used for tissue sections. Primary antibody binding was detected via corresponding Streptavidin Alexa Fluor 488-conjugated, goat anti-rabbit Alexa Fluor 555-conjugated, goat anti-rabbit Alexa Fluor 488-conjugated or donkey anti-goat Alexa Fluor 488 secondary antibodies (1:500; Invitrogen). Nuclei were counterstained with either Draq5 (Alexis Biochemicals) or PE (Vector Lab) to show nuclei. Staining was observed using a Leica TCS confocal microscope.

Figure 5B:
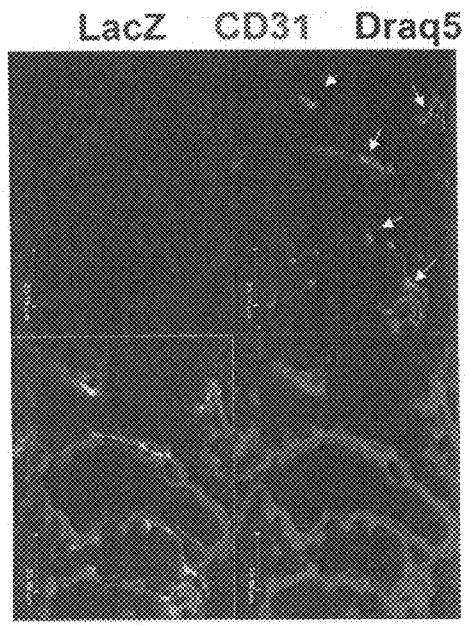
Figure 5C:
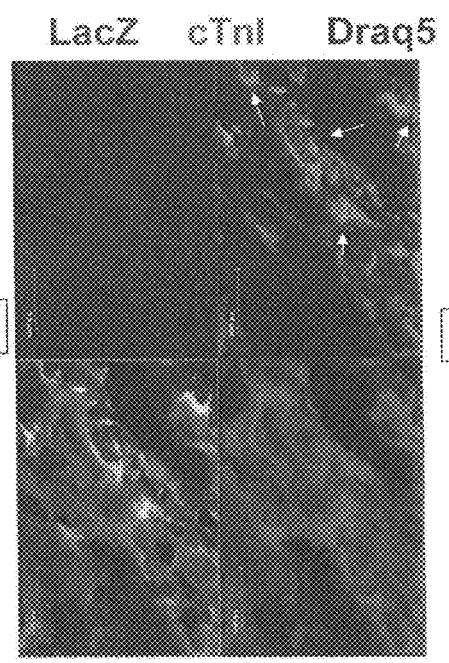
Figure 5D:

Donor cells were detected in the myocardium by laser confocal microscopy 1 month after cell transplantation. Double staining of sections for LacZ and cardiac-specific proteins indicated that LacZ colocalized with cTnI (FIG. 5B), indicating that Sca-1+ cells developed into cardiac myocyte-like cells after transplantation. Graft cells expressing β-gal also integrated into blood vessels and expressed endothelial cell marker-CD31 (FIG. 5C) and smooth muscle cell marker-smooth muscle α-actin (SM-actin) (FIG. 5D), demonstrating that grafted Sca-1+ cells also differentiated into endothelium and smooth muscle.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

REFERENCE LIST

1. American Heart Association. 2003 Heart and Stroke Statistical Update. 2002. Report
2. Tang Y L, Zhao Q, Zhang Y C, Cheng L, Liu M, Shi J, Yang Y Z, Pan C, Ge J, Phillips M I. Autologous mesenchymal stem cell transplantation induce VEGF and neovascularization in ischemic myocardium. *Regul Pept.* 2004; 117:3-10.
3. Tang Y L, Tang Y, Zhang Y C, Qian K, Shen L, Phillips M I. Improved graft mesenchymal stem cell survival in ischemic heart with a hypoxia-regulated heme oxygenase-1 vector. *J Am Coll Cardiol.* 2005; 46:1339-1350.
4. Tang Y L, Zhao Q, Qin X, Shen L, Cheng L, Ge J, Phillips M I. Paracrine action enhances the effects of autologous mesenchymal stem cell transplantation on vascular regeneration in rat model of myocardial infarction. *Ann Thorac Surg.* 2005; 80:229-236.
5. Tang Y L. Cellular therapy with autologous skeletal myoblasts for ischemic heart disease and heart failure. *Methods Mol. Med.* 2005; 112:193-204.
6. Yamada Y, Wang X D, Yokoyama S, Fukuda N, Takakura N. Cardiac progenitor cells in brown adipose tissue repaired damaged myocardium. *Biochem Biophys Res Commun.* 2006; 342:662-670.
7. Orlic D, Hill J M, Arai A E. Stem cells for myocardial regeneration. *Circ Res.* 2002; 91:1092-1102.
8. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P. Adult cardiac stem cells are multipotent and support myocardial regeneration. *Cell.* 2003; 114:763-776.
9. Oh H, Bradfute S B, Gallardo T D, Nakamura T, Gaussin V, Mishina Y, Pocius J, Michael L H, Behringer R R, Garry D J, Entman M L, Schneider M D. Cardiac progenitor cells from adult myocardium: homing, differentiation, and fusion after infarction. *Proc Natl Acad Sci USA.* 2003; 100:12313-12318.
10. Messina E, De Angelis L, Frati G, Morrone S, Chimenti S, Fiordaliso F, Salio M, Battaglia M, Latronico M V, Coletta M, Vivarelli E, Frati L, Cossu G, Giacomello A. Isolation and expansion of adult cardiac stem cells from human and murine heart. *Circ Res.* 2004; 95:911-921.
11. Wang X, Hu Q, Nakamura Y, Lee J, Zhang G, From A H, Zhang J. The Role of the Sca-1+/. *Stem Cells.* 2006; 24:1779-1788.
12. Tomita Y, Matsumura K, Wakamatsu Y, Matsuzaki Y, Shibuya I, Kawaguchi H, Ieda M, Kanakubo S, Shimazaki T, Ogawa S, Osumi N, Okano H, Fukuda K. Cardiac neural crest cells contribute to the dormant multipotent stem cell in the mammalian heart. *J Cell Biol.* 2005; 170:1135-1146.
13. Gude N, Muraski J, Rubio M, Kajstura J, Schaefer E, Anversa P, Sussman M. Akt Promotes Increased Cardiomyocyte Cycling and Expansion of the Cardiac Progenitor Cell Population. *Circ Res.* 2006.
14. Sakai T, Li R K, Weisel R D, Mickle D A, Jia Z Q, Tomita S, Kim E J, Yau T M. Fetal cell transplantation: a comparison of three cell types. *J Thorac Cardiovasc Surg.* 1999; 118:715-724.
15. Martin C M, Meeson A P, Robertson S M, Hawke T J, Richardson J A, Bates S, Goetsch S C, Gallardo T D, Garry D J. Persistent expression of the ATP-binding cassette transporter, Abcg2, identifies cardiac SP cells in the developing and adult heart. *Dev Biol.* 2004; 265:262-275.
16. Braunwald E, Bristow M R. Congestive heart failure: fifty years of progress. *Circulation.* 2000; 102: IV14-IV23.
17. Matsuura K, Nagai T, Nishigaki N, Oyama T, Nishi J, Wada H, Sano M, Toko H, Akazawa H, Sato T, Nakaya H, Kasanuki H, Komuro I. Adult cardiac Sca-1-positive cells differentiate into beating cardiomyocytes. *J Biol Chem.* 2004; 279:11384-11391.
18. Laugwitz K L, Moretti A, Lam J, Gruber P, Chen Y, Woodard S, Lin L Z, Cai C L, Lu M M, Reth M, Platoshyn O, Yuan J X, Evans S, Chien K R. Postnatal isl1+ cardioblasts enter fully differentiated cardiomyocyte lineages. *Nature.* 2005; 433:647-653.
19. Camelliti P, Borg T K, Kohl P. Structural and functional characterisation of cardiac fibroblasts. *Cardiovasc Res.* 2005; 65:40-51.
20. Fukuda K, Yuasa S. Stem cells as a source of regenerative cardiomyocytes. *Circ Res.* 2006; 98:1002-1013.
21. Xu M, Wani M, Dai Y S, Wang J, Yan M, Ayub A, Ashraf M. Differentiation of bone marrow stromal cells into the cardiac phenotype requires intercellular communication with myocytes. *Circulation.* 2004; 110:2658-2665.
22. Williams R L, Hilton D J, Pease S, Willson T A, Stewart C L, Gearing D P, Wagner E F, Metcalf D, Nicola N A, Gough N M. Myeloid leukaemia inhibitory factor maintains the developmental potential of embryonic stem cells. *Nature.* 1988; 336:684-687.

The invention claimed is:

1. A method of preparing a purified isolated cell population enriched in cardiac stem cells or cardiac progenitor cells, comprising:
    (a) obtaining a cardiac tissue sample that comprises (1) cardiac stem cells or cardiac progenitor cells and (2) fibroblasts; then
    (b) culturing said cardiac tissue sample for a time sufficient to allow the fibroblasts to adhere to the culture dish; then
    (c) collecting cells from the culture dish that migrate above the adhered fibroblasts of step (c); then
    (d) separating Sca-1-expressing cardiac stem cells or Sca-1-expressing cardiac progenitor cells from the collected cells; then
    (e) culturing the separated Sca-1-expressing cardiac stem cells or Sca-1-expressing cardiac progenitor cells in a cardiac fibroblast-conditioned medium in the absence of feeder cells;
    thereby obtaining a purified isolated cell population enriched in cardiac stem cells or cardiac progenitor cells.

2. The method of claim 1, wherein said cardiac tissue sample is an adult mammalian cardiac tissue sample.

3. The method of claim 1, wherein said cardiac tissue is subjected to enzymatic dissociation.

4. The method of claim 1, wherein said cardiac tissue is cultured for at least 10 days.

5. A method of preparing an isolated population of differentiated cells comprising:
    (a) preparing a purified isolated cell population enriched in cardiac stem cells or cardiac progenitor cells according to the method of claim 1; and
    (b) inducing said cardiac stem cells or cardiac progenitor cells to differentiate to cardiomvocytes, cardiac endothelial cells, cardiac smooth muscle cells, or cardiac neural crest cells, thereby obtaining an isolated population of differentiated cells.

6. The method of claim 5, wherein said cardiac stem cells are induced to differentiate by contacting said cardiac stem cells or cardiac progenitor cells with transforming growth factor β, bone morphogenic protein 2, bone morphogenic protein 4, and activin A.

7. A method of preparing a purified isolated cell population enriched in cardiac stem cells or cardiac progenitor cells, comprising:
    (a) obtaining cardiac tissue sample that comprises (1) cardiac stem cells or cardiac progenitor cells and (2) fibroblasts; then
    (b) culturing said cardiac tissue sample for a time sufficient to allow the fibroblasts to adhere to the culture dish; then
    (c) collecting cells from the culture dish that migrate above the adhered fibroblasts of step (c); then
    (d) separating Sca-1-expressing cardiac stem cells or Sca-1-expressing cardiac progenitor cells from the collected cells; then
    (e) cloning one or more cells isolated in step (e) to produce one or more clonogenic populations; then
    (f culturing said clonogenic populations in a cardiac fibroblast-conditioned medium in the absence of feeder cells;
    thereby obtaining a purified isolated cell population enriched in cardiac stem cells or cardiac progenitor cells.

* * * * *

UNITED STATES PATENT AND TRADEMARK OFFICE
CERTIFICATE OF CORRECTION

| | | |
|---|---|---|
| PATENT NO. | : 8,017,389 B2 | Page 1 of 1 |
| APPLICATION NO. | : 11/983431 | |
| DATED | : September 13, 2011 | |
| INVENTOR(S) | : Michael Ian Phillips et al. | |

It is certified that error appears in the above-identified patent and that said Letters Patent is hereby corrected as shown below:

<u>Column 30, Line 38:</u>
"cells to differentiate to cardiomvocytes, cardiac endothelial" should read, --cells to differentiate to cardiomyocytes, cardiac endothelial--.

Signed and Sealed this
Twenty-fourth Day of January, 2012

David J. Kappos
*Director of the United States Patent and Trademark Office*